US011873305B2

(12) United States Patent
Zhang et al.

(10) Patent No.: US 11,873,305 B2
(45) Date of Patent: Jan. 16, 2024

(54) PROCESSES FOR SYNTHESIS OF SUBSTITUTED INDOLE INTERMEDIATES FOR THE SYNTHESIS OF SERD COMPOUNDS

(71) Applicants: Genentech, Inc., South San Francisco, CA (US); Hoffmann-La Roche Inc., Little Falls, NJ (US)

(72) Inventors: Haiming Zhang, San Mateo, CA (US); Jie Xu, San Mateo, CA (US); Georg Wuitschik, Basel (CH); Remy Angelaud, San Francisco, CA (US); Sebastian Herold, Bad Saeckingen (DE); Alfred Stutz, Zurich (CH); Tobias Bruetsch, Dietikon (CH); Johannes Burkhard, Zurich (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/360,593

(22) Filed: Jun. 28, 2021

(65) Prior Publication Data

US 2022/0002304 A1 Jan. 6, 2022

Related U.S. Application Data

(60) Provisional application No. 63/046,216, filed on Jun. 30, 2020.

(51) Int. Cl.
*C07D 209/10* (2006.01)
*C07D 487/04* (2006.01)

(52) U.S. Cl.
CPC .................................. *C07D 487/04* (2013.01)

(58) Field of Classification Search
CPC .................................................... C07D 209/10
USPC .......................................................... 548/469
See application file for complete search history.

(56) References Cited

U.S. PATENT DOCUMENTS

| | | | |
|---|---|---|---|
| 9,980,947 | B2 | 5/2018 | Labadie et al. |
| 10,954,234 | B2 | 3/2021 | Chung et al. |
| 10,966,963 | B2 | 4/2021 | Labadie et al. |
| 2021/0236473 | A1 | 8/2021 | Labadie et al. |
| 2022/0002304 | A1 | 1/2022 | Zhang et al. |
| 2022/0041587 | A1 | 2/2022 | Chung et al. |

FOREIGN PATENT DOCUMENTS

| | | | |
|---|---|---|---|
| WO | 98/30541 | A1 | 7/1998 |
| WO | 2019/245974 | A1 | 12/2019 |

OTHER PUBLICATIONS

Buckley et al., "Observations on the modified Wenker synthesis of aziridines and the development of a biphasic system" J. Org. Chem. 78(3):1289-1292. ( 2013).

Park et al., "Synthesis of optically active 2-alkyl-3,4-iminobutanoic acids. Beta-amino acids containing an aziridine heterocycle" J. Org.Chem. 66:3696-3703 ( 2001).

Invitation to Pay Additional Fees and, Where Applicable Protest Fee with Annex to Form PCT/ISA/206 Communication Relating to the Results of the Partial International Search—PCT/US2021/039325 dated Oct. 25, 2021.

*Primary Examiner* — Douglas M Willis
(74) *Attorney, Agent, or Firm* — Genentech, Inc.

(57) ABSTRACT

Provided herein are processes for the preparation of indolyl intermediates using Wenker Synthesis for the total synthesis of SERD compounds useful in the treatment of cancer.

25 Claims, No Drawings

PROCESSES FOR SYNTHESIS OF SUBSTITUTED INDOLE INTERMEDIATES FOR THE SYNTHESIS OF SERD COMPOUNDS

CROSS REFERENCE TO RELATED APPLICATIONS

This application claims the benefit of U.S. Provisional Patent Application No. 63/046,216, filed 30 Jun. 2020, and is incorporated herein by reference in its entirety and for all purposes.

FIELD OF INVENTION

Provided herein are processes for synthesis of GDC-9545 and intermediates related to large scale manufacture of (R)-1-(1H-indol-3-yl)propan-2-amine and (R)-3-((1-(1H-indol-3-yl)propan-2-yl)amino)-2,2-difluoropropan-1-ol.

BACKGROUND

Fused tricyclic compounds comprising a substituted phenyl or pyridinyl moiety within the scope of the present disclosure are useful as estrogen receptor ("ER") targeting agents.

The ER is a ligand-activated transcriptional regulatory protein that mediates induction of a variety of biological effects through its interaction with endogenous estrogens. Endogenous estrogens include 170 (beta)-estradiol and estrones. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. ER-α targeting agents have particular activity in the setting of metastatic disease and acquired resistance. ER-α targeting agents are disclosed in U.S. Publication Number 2016/0175289.

Useful processes for preparing fused tricyclic compounds such as GDC-9545 comprising a substituted phenyl or pyridinyl moiety are disclosed in U.S. Pat. No. 9,980,947 and U.S. Patent Publication Number US2020/0002331. However, it is known that scale-up of chemical processes can result in unexpected conditions such as, for example, increased impurities or decreased yields. Accordingly, there is a need for improved processes for the synthesis of GDC-9545 that increase yields and/or decrease impurities. As compared to currently known processes, the processes of the present disclosure advantageously provide improvements in, for example, process conditions, reagent selection, complexity of required unit operations, scalability, and the like.

SUMMARY

Provided herein are solutions to these problems and more.

In one aspect provided herein is a process for the preparation of a compound of formula (II) as described herein, the process comprising (a) contacting a compound of formula (III) as described herein with a sulfonic acid to form a compound of formula (IIIa) as described herein; (b) contacting the compound of formula (IIIa) with a base to form compound of formula (IV) as described herein; hydrogenating the compound of formula (IV) to form a compound of formula (V) as described herein; and contacting the compound of formula (V) with a compound of formula (VI) described herein, thereby synthesizing the compound of formula (II).

In another aspect provided herein is a process for the preparation of a compound of formula (II) as described herein, the process comprising (a) contacting a compound of formula (VII) as described herein with a compound of formula (VI) as described herein to make a compound of formula (VIIa) as described herein; (b) contacting the compound of formula (VIIa) with an acid thereby synthesizing a compound of formula (VIIb) as described herein; contacting the compound of formula (VIIb) with 1,1'-carbonyldiimidazole thereby synthesizing a compound of formula (VIIc) as described herein; contacting the compound of formula (VIIc) with a compound of formula (VIII) as described herein to make a compound of formula (Va) as described herein; and contacting the compound of formula (Va) with a base followed by an acid thereby making the compound of formula (II).

In another aspect provided herein is a process for the preparation of a compound of formula (II) as described herein, the process comprising contacting a compound of formula (V) as described herein with a compound of formula (VI) as described herein, wherein the compound of formula (V) is prepared by: (a) contacting a compound of formula (VIIp) as described herein with a compound of formula (VIII) as described herein to make a compound of formula (Vb) as described herein; and (b) contacting the compound of formula (Vb) with an acid thereby making the compound of formula (V).

In another aspect provided herein is a process for the preparation of a compound of formula (II), the process comprising (a) contacting alanine with a compound of formula (IX) as described herein to form a compound of formula (XI) as described herein; b) contacting the compound of formula (XI) with a chlorinating agent, a compound of formula

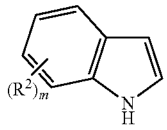

, and an organoaluminum compound to form a compound of formula (Vc) as described herein; and (c) contacting the compound of formula (Vc) with a reducing agent thereby forming a compound of formula (II).

In another aspect provided herein is a process for the synthesis of a compound of formula (1), the process comprising contacting a compound of formula (2) (synthesized according to any of the processes described herein) with a compound of formula (10).

In one aspect provided herein is a method of treating cancer by administering an effective amount of a compound of formula (I) or pharmaceutically acceptable salt thereof synthesized according to any of the processes described herein to a patient having cancer.

In another aspect provided herein is a method of treating lung cancer, ovarian cancer, endometrial cancer, prostate cancer, uterine cancer, or breast cancer by administering an effective amount of a compound of formula (I) or pharmaceutically acceptable salt thereof synthesized according to any of the processes described herein to a patient having said cancer.

In another aspect provided herein are methods of treating breast cancer in a patient having breast cancer by administering an effective amount of a compound of formula (I) or pharmaceutically acceptable salt thereof synthesized according to any of the processes described herein.

DETAILED DESCRIPTION

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, the term "alkyl" refers to an aliphatic straight-chain or branched-chain saturated hydrocarbon moiety having 1 to 20 carbon ($C_{1-20}$) atoms. In particular embodiments the alkyl has 1 to 10 carbon ($C_{1-10}$) atoms. In particular embodiments the alkyl has 1 to 6 carbon ($C_{1-6}$) atoms. In particular embodiments the alkyl has 1 to 4 carbon ($C_{1-4}$) atoms. In particular embodiments the alkyl has 1 to 3 carbon ($C_{1-3}$) atoms. Alkyl groups may be optionally substituted independently with one or more substituents described herein.

As used herein, the term "substituted" refers to the replacement of at least one of hydrogen atom of a compound or moiety with another substituent or moiety. Examples of such substituents include, without limitation, halogen, —OH, —CN, oxo, alkoxy, alkyl, alkylene, aryl, heteroaryl, haloalkyl, haloalkoxy, cycloalkyl and heterocycle. In one embodiment, substituted as used herein can refer to replacement of at least one hydrogen atom of a compound or moiety described herein with halogen or alkyl.

As used herein, the term "alkoxy" refers to a group of the formula —O—R', wherein R' is an alkyl group. Alkoxy groups may be optionally substituted independently with one or more substituents described herein. Examples of alkoxy moieties include methoxy, ethoxy, isopropoxy, and tert-butoxy.

As used herein, the term "haloalkyl" refers to an alkyl group wherein one or more of the hydrogen atoms of the alkyl group has been replaced by the same or different halogen atoms, particularly fluorine and/or chlorine atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl or trifluoromethyl.

As used herein, the terms "halo" and "halogen" are interchangeably and refer to a substituent fluorine, chlorine, bromine, or iodine.

As used herein, the term "cycloalkyl" means a saturated or partially unsaturated carbocyclic moiety having mono-, bi- (including bridged bicyclic) or tricyclic rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_8$)cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl), bicyclo[3.1.0]hexanyl, bicyclo[3.1.0]hexenyl, bicyclo[3.1.1]heptanyl, and bicyclo [3.1.1]heptenyl. The cycloalkyl moiety can be attached in a "spirocycloalkyl" fashion such as "spirocyclopropyl":

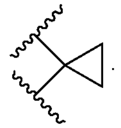 [SMILES: *C1(*)CC1]

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer.

The term "effective amount" or "therapeutically effective amount" refers to an amount of a compound described herein capable of treating or preventing a disorder, disease or condition, or symptoms thereof, disclosed herein.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for cancer.

As used herein, the terms "moiety" and "substituent" refer to an atom or group of chemically bonded atoms that is attached to another atom or molecule by one or more chemical bonds thereby forming part of a molecule.

An "inorganic acid" refers to acids such as, but not limited to, hydrochloric acid, hydrobromic acid, hydroiodic acid, sulfuric acid, sulfamic acid, nitric acid, boric acid, phosphoric acid, and combinations thereof.

An "organic acid" refers to acids such as, but not limited to: acetic acid; trifluoroacetic acid; phenylacetic acid; propionic acid; stearic acid; lactic acid; ascorbic acid; maleic acid; hydroxymaleic acid; isethionic acid; succinic acid; valeric acid; fumaric acid; malonic acid; pyruvic acid; oxalic acid; glycolic acid; salicylic acid; oleic acid; palmitic acid; lauric acid; a pyranosidyl acid, such as glucuronic acid or galacturonic acid; an alpha-hydroxy acid, such as mandelic acid, citric acid, or tartaric acid; cysteine sulfinic acid; an amino acid, such as aspartic acid, glutaric acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, benzenesulfonic acid or ethanesulfonic acid; cysteine sulfonic acid; and combinations thereof.

The terms "inorganic base" and "hydroxide base" are used interchangeably and refer to bases such as, but not limited to, sodium hydroxide, potassium hydroxide, lithium hydroxide, ammonium hydroxide, magnesium hydroxide, sodium carbonate, potassium carbonate, and combinations thereof. In certain embodiments, the inorganic base is an alkali-metal base (e.g. NaOH, KOH, or LiOH).

An "organic base" refers to an organic compound containing one or more nitrogen atoms, and which acts as a base. Examples of organic bases include, but are not limited to, tertiary amine bases. Examples of organic bases include, but are not limited to, 1,8-Diazabicyclo[5.4.0]undec-7-ene ("DBU"), N-methyl-morpholine (NM M), diisopropylethylamine (DIPEA), triethylamine (TEA), a t-butoxide (e.g., sodium, potassium, calcium or magnesium tert-butoxide).

Compounds described herein may be present in a salt form that encompasses pharmaceutically acceptable salts and non-pharmaceutically acceptable salts. As used herein, the term "pharmaceutically acceptable salts" refers to those salts that retain the biological effectiveness and properties of the free bases or free acids, which are not biologically or otherwise undesirable. In addition to pharmaceutically acceptable salts, the compounds of the present disclosure may be in the form of non-pharmaceutically acceptable salts that can be useful as an intermediate for isolating or purifying said compounds.

Exemplary acid salts of the compounds of the present disclosure include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Exemplary base salts of the compounds of the present disclosure include, but are not limited to, inorganic salts formed from sodium, potassium, ammonium, calcium, magnesium, iron, zinc, copper, manganese, and aluminum cations. Organic salts formed from cations including primary, secondary, and tertiary amines; substituted amines including naturally occurring substituted amines; cyclic amines; basic ion exchange resins; isopropylamine; trimethylamine; diethylamine; trimethylamine; tripropylamine; ethanolamine; 2-diethylaminoethanol; trimethamine; dicyclohexylamine; lysine; arginine; histidine; caffeine; procaine; hydrabamine; choline; betaine; ethylenediamine; glucosamine; methylglucamine; theobromine; purines; piperazine; piperidine; N-ethylpiperidine; and polyamine resins.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers, which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". In certain embodiments, the compound is enriched by at least about 90% by weight with a single diastereomer or enantiomer. In other embodiments the compound is enriched by at least about 95%, 98%, or 99% by weight with a single diastereomer or enantiomer.

Certain compounds and pharmaceutically acceptable salts thereof described herein possess asymmetric carbon atoms (optical centers) or double bonds; the racemates, diastereomers, regioisomers and individual isomers (e.g., separate enantiomers) are all intended to be encompassed within the scope of the present disclosure.

The compounds and pharmaceutically acceptable salts thereof described herein may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative while stereochemistry is definitively established, such as from x-ray crystallographic data.

Provided herein are processes for the preparation of compounds useful in the treatment of cancer. Compounds of formula (I), including compound 1 and compound A, are exemplified in, for example, U.S. Pat. No. 9,980,947 and U.S. Patent Publication Number US2020/0002331. The processes described herein improve product purity and yields of the final products as well as key intermediates in the synthesis thereof.

Provided herein are processes for the preparation of a compound of formula (II) or a salt thereof:

(II)

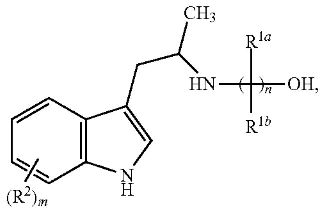

wherein each of $R^{1a}$ and $R^{1b}$ is independently hydrogen, halogen, unsubstituted $C_{1-3}$ alkyl, unsubstituted $C_{1-3}$ haloalkyl, unsubstituted $C_{1-3}$ alkoxy, —CN, unsubstituted $C_{3-6}$ cycloalkyl, or unsubstituted $C_{3-6}$ spirocycloalkyl;

each $R^2$ is independently halogen, hydroxyl, —CN, unsubstituted $C_{1-3}$ alkyl, unsubstituted $C_{1-3}$ haloalkyl, or unsubstituted $C_{1-3}$ alkoxy;

m is 0, 1 or 2; and n is 1, 2, or 3.

In one aspect provided herein is a process (P1) for the preparation of a compound of formula (II) or a salt thereof where the process comprises the steps:

(a) contacting a compound of formula (III) or a salt thereof, (III)

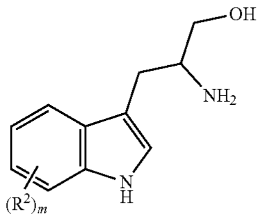

with a sulfonic acid to form a compound of formula (IIIa) or a salt thereof;

(IIIa)

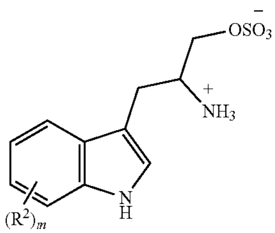

(b) contacting the compound of formula (IIIa) or a salt thereof with a base to form compound of formula (IV) or a salt thereof;

(IV)

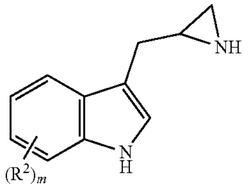

(c) hydrogenating the compound of formula (IV) or a salt thereof to form a compound of formula (V) or a salt thereof; and (V)

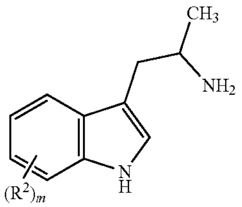

(d) contacting the compound of formula (V) or a salt thereof with a compound of formula (VI);

(VI)

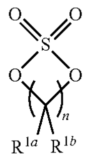

wherein $R^{1a}$ and $R^{1b}$ are as described herein, thereby forming a compound of formula (II).

In one embodiment of the process (P1) described herein, the compound of formula (III) is a salt of formula:

(III*)

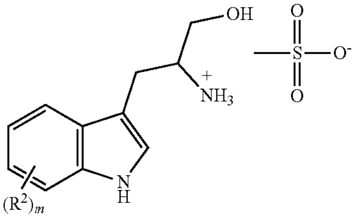

In one such embodiment, the salt is a mesylate ($MeSO_3$) salt.

In one embodiment of the process (P1) described herein, the compound of formula (III) has formula:

(3)

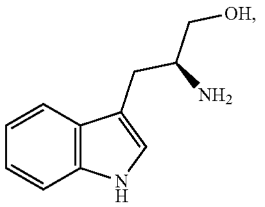

(3x)

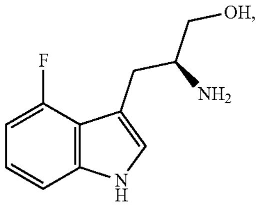

(3y)

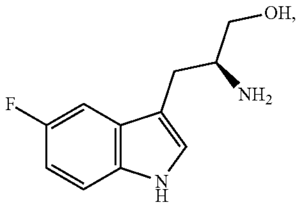

or (3z)

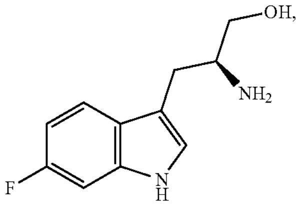

or a stereoisomer or salt thereof.

In one embodiment of the process (P1) described herein, the compound of formula (III) has formula:

(3*)

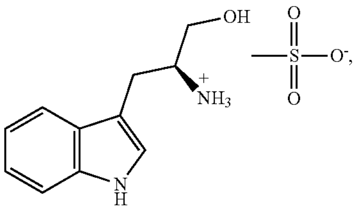

(3x*)

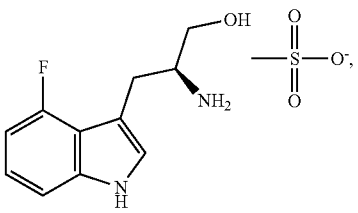

-continued (3y*)

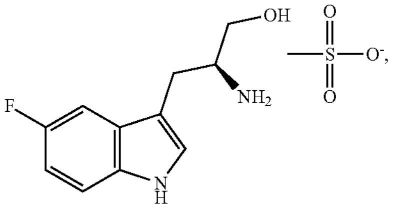

or (3z*)

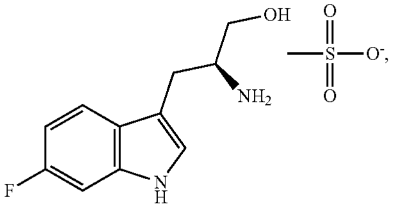

or a stereoisomer or salt thereof.

In one embodiment of the process (P1) described herein, the compound of formula (IIIa) has formula:

(3a)

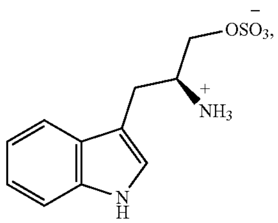

(3a1)

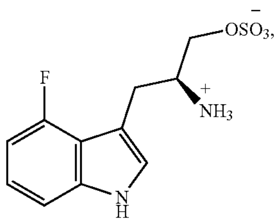

(3a2)

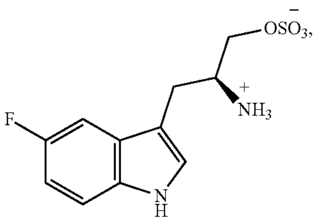

or (3a3)

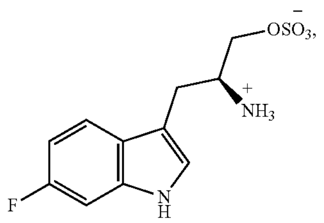

or a stereoisomer or salt thereof.

In one embodiment of the process (P1) described herein, the compound of formula (IV) has formula:

(4)

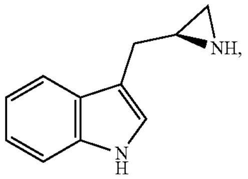

(4a)

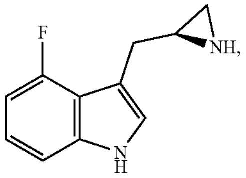

(4b)

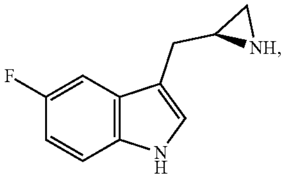 or (4c)

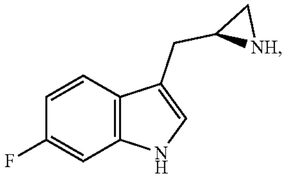

or a stereoisomer or salt thereof.

In one embodiment of the process (P1) described herein, the compound of formula (IV) has formula:

(4)

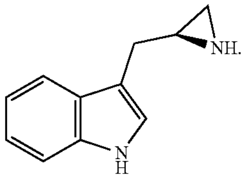

In one embodiment of the process (P1) described herein, the sulfonic acid is $H_2SO_4$ or $ClSO_3H$. In another embodiment, the sulfonic acid is $H_2$ $SO_4$. In still another embodiment, the sulfonic acid is $ClSO_3H$.

In one embodiment of the process (P1) described herein, the base is an alkali-metal hydroxide base. In one embodiment, the base is a hydroxide base. In one embodiment, the base is KOH, NaOH, or LiOH. In one preferred embodiment, the base is NaOH or KOH. In one embodiment, the base is NaOH.

In one embodiment of the process (P1) described herein, the hydrogenation of step (c) is performed using a catalyst comprising Pd, Pt, or Ni. In one such embodiment, the catalyst is Pd/C, Pt/C, or Raney Ni. In another such embodiment, the catalyst is a Pd catalyst selected from the group consisting of $Pd(OH)_2$, $Pd(OAc)_2$, $PdCl_2$, $PdCl_2(MeCN)_2$, $Pd(dba)_2$, $Pd_2(dba)_3$, $Pd(TFA)_2$, $[Pd(allyl)Cl]_2$, $[Pd(cinammyl)Cl]_2$, and (η3-Allyl)(η5-cyclopentadienyl)palladium(II). In one embodiment, the Pd catalyst is $Pd(OH)_2$.

In another embodiment of the process (P1) described herein, the hydrogenation of step (c) is performed using catalytic transfer hydrogenation in the presence of isopropanol, formic acid, formate, or ammonium.

In another embodiment of the process (P1) described herein, the compound of formula (V) has formula:

(5)

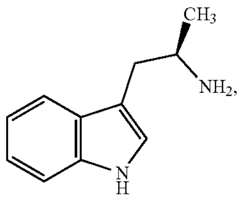

(5x)

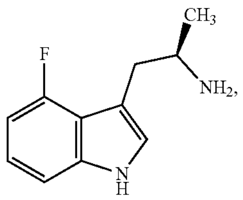

(5y)

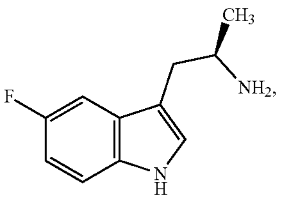 or (5z)

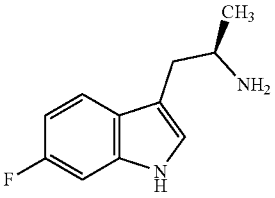

or a stereoisomer or salt thereof.

In another such embodiment of the process of P1, the compound of formula (III) is a compound of formula (3*); the compound of formula (IIIa) is a compound of formula (3a); the compound of formula (IV) is a compound of formula (4); and the compound of formula (V) is a compound of formula (5).

In another such embodiment of the process of P1, the compound of formula (III) is a compound of formula (3x*); the compound of formula (IIIa) is a compound of formula (3a1); the compound of formula (IV) is a compound of formula (4a); and the compound of formula (V) is a compound of formula (5x).

In another such embodiment of the process of P1, the compound of formula (III) is a compound of formula (3y*); the compound of formula (IIIa) is a compound of formula (3a2); the compound of formula (IV) is a compound of formula (4b); and the compound of formula (V) is a compound of formula (5y).

In another such embodiment of the process of P1, the compound of formula (III) is a compound of formula (3z*); the compound of formula (IIIa) is a compound of formula (3a3); the compound of formula (IV) is a compound of formula (4c); and the compound of formula (V) is a compound of formula (5z).

Further provided herein is a process (P2) for the preparation of a compound of formula (II), where the process comprises:

(a) contacting a compound of formula (VII) or a stereoisomer or salt thereof, (VII)

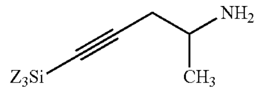

wherein each Z is independently $C_{1-3}$ alkyl or phenyl, with a compound of formula (VI), (VI)

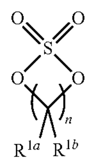

wherein $R^{1a}$ and $R^{1b}$ are as described herein, thereby synthesizing a compound of formula (VIIa) or a salt thereof;

(VIIa)

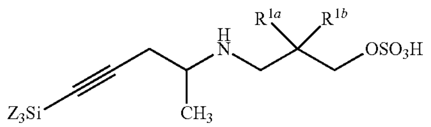

(b) contacting a compound of formula (VIIa) or a stereoisomer or salt thereof with an acid thereby synthesizing a compound of formula (VIIb) or a salt thereof;

(VIIb)

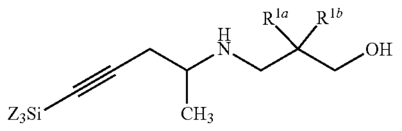

(c) contacting the compound of formula (VIIb) or a stereoisomer or salt thereof with 1,1'-carbonyldiimidazole thereby synthesizing a compound of formula (VIIc) or a salt thereof;

(VIIc)

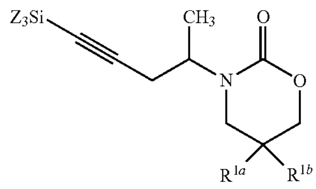

(d) contacting the compound of formula (VIIc) or a stereoisomer or salt thereof with a compound of formula (VIII) or a salt thereof, (VIII)

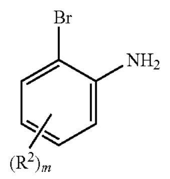

wherein $R^2$ and m are as described herein, to make a compound of formula (Va) or a salt thereof; and (Va)

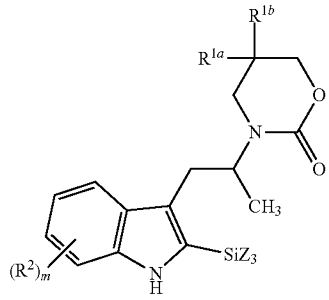

(e) contacting the compound of formula (Va) or a stereoisomer or salt thereof with a base followed by an acid thereby making the compound of formula (II) or a stereoisomer or salt thereof.

In one embodiment of the process described herein, $R^2$ is halogen and m is 1. In another embodiment, $R^2$ is F and m is 1. In one preferred embodiment, m is 0.

In one embodiment of the process (P2) described herein, step (a) further comprises deprotecting a compound of formula (VIIp)

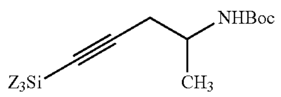

or a stereoisomer or salt thereof to make the compound of formula (VII) or a salt thereof.

In one embodiment of the process (P2) described herein, the compound of formula (Va) has formula:

(5a-1)

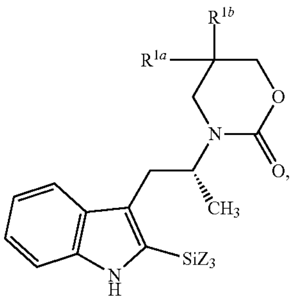

-continued (5a1-1)

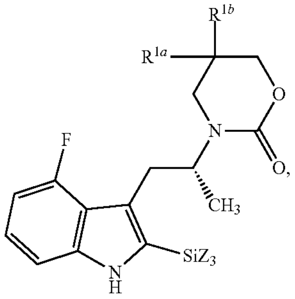

(5a2-1)

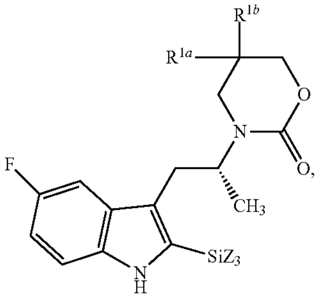

or (5a3-1)

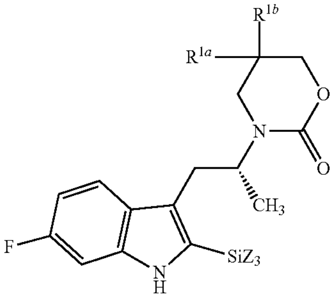

or a salt thereof.

In one embodiment of the process (P2) described herein, the compound of formula (Va) has formula:

(5a)

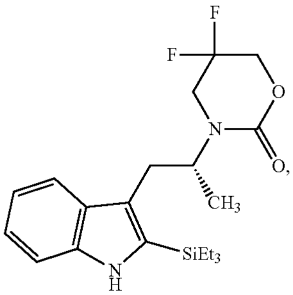

-continued (5a1)

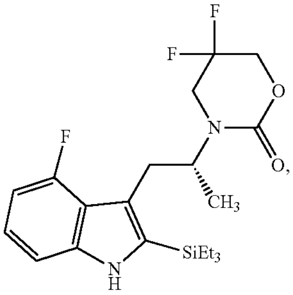

(5a2)

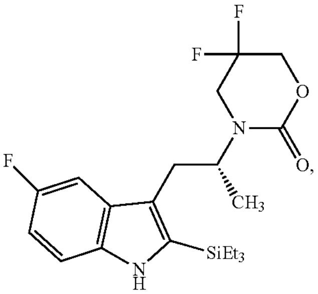

or (5a3)

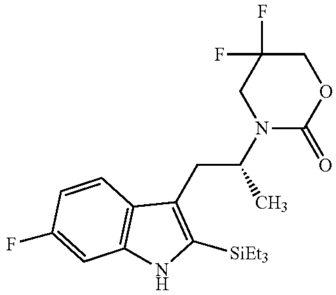

or a salt thereof.

In one embodiment of the process (P2) described herein, each Z is independently $C_{1-4}$ alkyl. In another embodiment, each Z is methyl, each Z is ethyl, each Z is isopropyl or wherein $SiZ_3$ is $Si(PhMe_2)$ or $Si(t\text{-}BuMe_2)$. In another embodiment, each Z is ethyl.

In one embodiment of the process (P2) described herein, the compound of formula (VII) has formula:

(7)

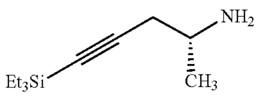

or a salt thereof.

In one embodiment of the process (P2) described herein, the compound of formula (VIIa) has formula:

(7a)

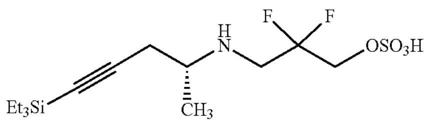

or a salt thereof.

In one embodiment of the process (P2) described herein, the compound of formula (VIIb) has formula:

(7b)

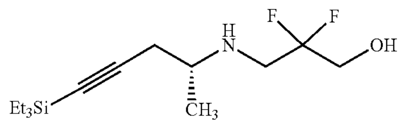

or a salt thereof.

In one embodiment of the process (P2) described herein, the compound of formula (VIIc) has formula:

(7c)

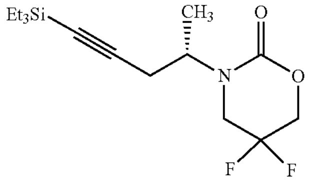

or a salt thereof.

In one embodiment of the process (P2) described herein, the compound of formula (VIII) has formula:

(8)

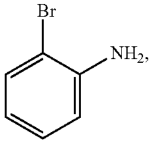

(8a)

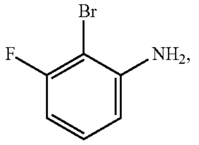

(8b)

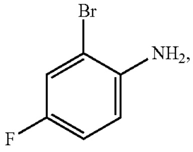

or (8c)

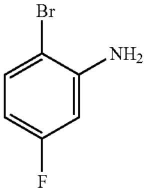

or a salt thereof.

In one embodiment of the process (P2) described herein, the acid of step (b) is an inorganic acid. In one such embodiment, the acid is $H_2SO_4$.

In one embodiment of the process (P2) described herein, the base of step (e) is an inorganic base such as NaOH, KOH, or LiOH. In one such embodiment, the base of step (e) is LiOH. In one embodiment of the process (P2) described herein, the acid of step (e) is an inorganic acid. In one such embodiment, the acid is HCl.

In one embodiment of the process (P2) described herein, step (d) further comprises a palladium catalyst. In one such embodiment, the palladium catalyst is $Pd(dppf)Cl_2 \cdot DCM$. In one embodiment of the process (P2) described herein, the acid is HCl.

In one embodiment of the process (P2) described herein, the process comprises synthesizing a compound of formula (2) or a salt thereof, the process comprising:

(a) contacting the compound of formula (7) or a salt thereof with a compound of formula (6) to make a compound of formula (7a) or a salt thereof;

(b) contacting the compound of formula (7a) or a salt thereof with an acid as described herein thereby synthesizing a compound of formula (7b) or a salt thereof;

(c) contacting the compound of formula (7b) or a salt thereof with 1,1'-carbonyldiimidazole thereby synthesizing a compound of formula (7c) or a salt thereof;

(d) contacting the compound of formula (7c) or a salt thereof with a compound of formula (8) or a salt thereof in the presence of a Pd catalyst described herein thereby synthesizing a compound of formula (5a) or a salt thereof; and (e) contacting the compound of formula (5a) or a salt thereof with a base as described herein followed by an acid as described herein thereby synthesizing a compound of formula (2) or a salt thereof.

Further provided herein is a process (P3) for the preparation of a compound of formula (II) or a salt thereof, where the process comprises contacting a compound of formula (V), (V)

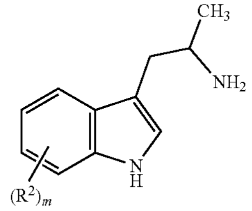

or a salt thereof wherein $R^2$ and m are as described herein, with a compound of formula (VI), (VI)

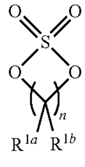

wherein $R^{1a}$ and $R^{1b}$ are as described herein and wherein the compound of formula (V) or a salt thereof is prepared by:

(a) contacting a compound of formula (VIIp), (VIIp)

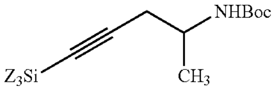

or a stereoisomer or salt thereof, wherein each Z is as described herein, with a compound of formula (VIII), (VIII)

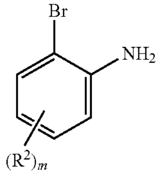

or a salt thereof, thereby synthesizing a compound of formula (Vb); and (Vb)

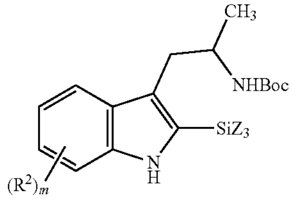

(b) contacting the compound of formula (Vb) or a stereoisomer or salt thereof with an acid thereby making the compound of formula (V) or a salt thereof.

In one embodiment of the process (P3) described herein, each Z is ethyl. In one embodiment of the process (P3) described herein, m is 0. In one embodiment of the process (P3) described herein the acid of step b is an inorganic acid. In one such embodiment, the acid is HCl.

In one embodiment, the compound of formula (VIIp) has formula;

(7p)

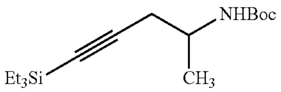

In one embodiment of the process (P3) described herein, step (a) further comprises a palladium catalyst. In one such embodiment, the palladium catalyst is $Pd(dppf)Cl_2 \cdot DCM$.

In one embodiment of the process (P3) described herein, the compound of formula (Vb) has formula:

(5b-1)

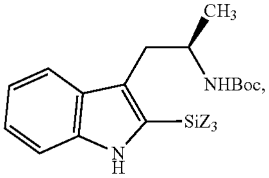

(5b1-1)

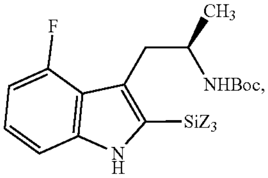

-continued (5b2-1)

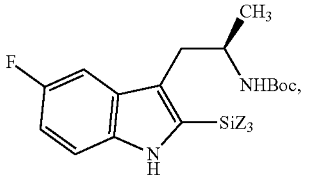

or (5b3-1)

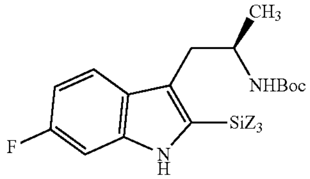

or a salt thereof.

In one embodiment of the process (P3) described herein, the compound of formula (Vb) has formula:

(5b)

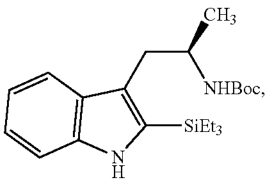

(5b1)

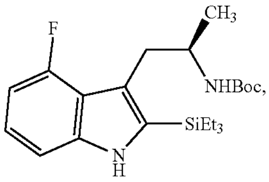

(5b2)

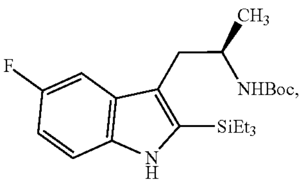

or (5b3)

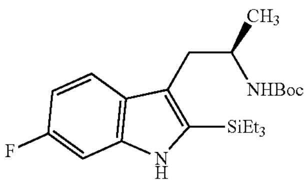

or a salt thereof.

In one embodiment of the process (P1), (P2), and (P3) described herein, the compound of formula (VI) comprises formula:

(6)

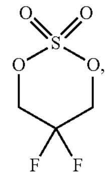

(6a)

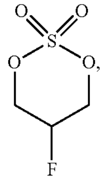

(6b)

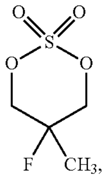

(6c)

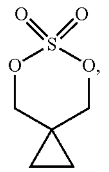

(6d)

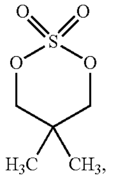

(6e)

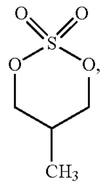

(6f)

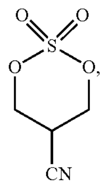

(6g)

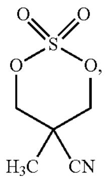

-continued (6h)

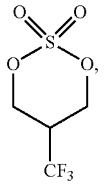

(6i)

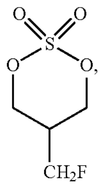

or (6j)

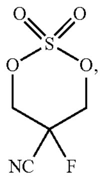

or a stereoisomer thereof.

In one embodiment of the process (P1), (P2), and (P3) described herein, the compound of formula (VI) comprises formula (6), (6a), or (6b). In one embodiment of the process (P1), (P2), and (P3) described herein, the compound of formula (VI) comprises formula (6c), (6d), or (6e). In one embodiment of the process (P1), (P2), and (P3) described herein, the compound of formula (VI) comprises formula (6f), (6g), (6h), (6i), or (6j). In one embodiment of the process (P1), (P2), and (P3) described herein, the compound of formula (VI) comprises formula (6).

Further provided herein is a process (P4) for the preparation of a compound of formula (II) or a salt thereof, the process comprising the steps:

(a) contacting alanine with a compound of formula (IX), (IX)

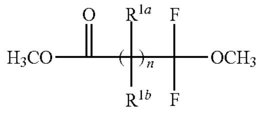

wherein $R^{1a}$, $R^{1b}$, and n are as described herein, to form a compound of formula (XI);

(XI)

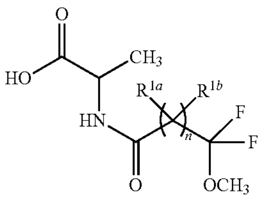

or a salt thereof (b) contacting the compound of formula (XI) or a salt thereof with (i) a chlorinating agent, (ii) a compound of formula

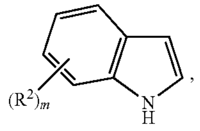

wherein $R^2$ and m are as described herein, and (iii) an organoaluminum compound to form a compound of formula (Vc); and (Vc)

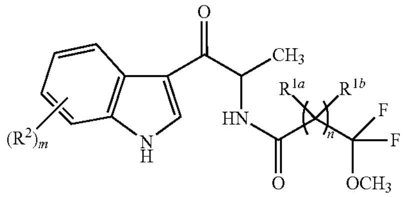

or a salt thereof (c) contacting the compound of formula (Vc) or a salt thereof with a reducing agent thereby forming a compound of formula (II) or a salt thereof.

In one embodiment of the process (P4) described herein, the organoaluminum compound has the formula $X_3Al$, where X is independently Cl or $C_{1-4}$ alkyl. In one such embodiment, X is independently methyl, ethyl, n-propyl, isopropyl, n-butyl, or isobutyl. In another embodiment of the process (P4) described herein, the organoaluminum compound is trimethyl aluminum, Methyl aluminum, triisobutyl aluminum, dimethyl aluminum chloride, diethyl aluminum chloride, or ethyl aluminum dichloride. In one such embodiment, the organoaluminum compound is trimethyl aluminum.

In one embodiment of the process (P4) described herein, the reducing agent is sodium aluminum hydride or sodium bis(2-methoxyethoxy)aluminum dihydride. In one such embodiment, the reducing agent is sodium aluminum hydride. In one such embodiment, the reducing agent is sodium aluminum hydride in the presence of methanol.

In one embodiment of the process (P4) described herein, the chlorinating agent is $SOCl_2$, methyl chloroformate, ethyl chloroformate, isobutyl chloroformate, pivaloyl chloride, or oxalyl chloride. In one such embodiment, the chlorinating agent is oxalyl chloride. In another such embodiment, the chlorinating agent is oxalyl chloride in the presence of N-formyl pyrrolidine or N,N-dimethylformamide.

In one embodiment of the process (P4) described herein, the compound of formula (IX) has formula:

(9)

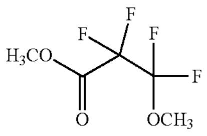

or a salt thereof.

In one embodiment of the process (P4) described herein, the compound of formula (Xi) has formula:

(11)

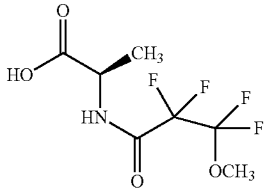

or a salt thereof.

In one embodiment of the process (P4) described herein, the indole of step b) has formula:

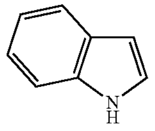,
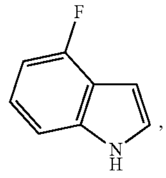,
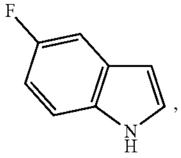, or
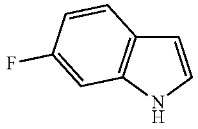.

or a salt thereof.

In one embodiment of the process (P4) described herein, the compound of formula (Vc) has formula:

(5c)

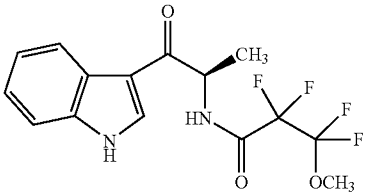

or a salt thereof.

In one embodiment of the processes described herein, each of $R^{1a}$ and $R^{1b}$ is independently hydrogen, halogen, unsubstituted $C_{1-3}$ alkyl, unsubstituted $C_{1-3}$ haloalkyl, or unsubstituted $C_{1-3}$ alkoxy.

In one embodiment of the processes described herein, each of $R^{1a}$ and $R^{1b}$ is independently hydrogen, halogen, or unsubstituted $C_{1-3}$ alkyl.

In one embodiment of the processes described herein, $R^{1a}$ and $R^{1b}$ are independently hydrogen, halogen, cyano, unsubstituted $C_{1-3}$ alkyl, or cyclopropyl. In another embodiment of the processes described herein, $R^{1a}$ and $R^{1b}$ are independently hydrogen, halogen, or methyl. In another embodiment of the processes described herein, $R^{1a}$ is hydrogen and $R^{1b}$ is halogen, methyl, cyano, or cyclopropyl. In still another embodiment of the processes described herein, $R^{1a}$ is hydrogen and $R^{1b}$ is halogen. In still another embodiment of the processes described herein, $R^{1a}$ is hydrogen and $R^{1b}$ is methyl. In still another embodiment of the processes described herein, $R^{1a}$ is methyl and $R^{1b}$ is halogen, methyl, cyano, or cyclopropyl. In another embodiment of the processes described herein, $R^{1a}$ is halogen and $R^{1b}$ is halogen, methyl, cyano, or cyclopropyl.

In one embodiment of the processes described herein, $R^{1a}$ and $R^{1b}$ are independently halogen, or methyl. In another embodiment of the processes described herein, $R^{1a}$ is halogen and $R^{1b}$ is methyl. In one preferred embodiment of the processes described herein, $R^{1a}$ is halogen and $R^{1b}$ is halogen. In a preferred embodiment of the processes described herein, $R^{1a}$ and $R^{1b}$ are F.

In one embodiment of the processes described herein, each of $R^{1a}$ and $R^{1b}$ is independently hydrogen, halogen, unsubstituted $C_{1-3}$ alkyl, unsubstituted $C_{1-3}$ haloalkyl, or unsubstituted $C_{1-3}$ alkoxy.

In one embodiment of the processes described herein, each of $R^{1a}$ and $R^{1b}$ is unsubstituted $C_{3-6}$ cycloalkyl or unsubstituted $C_{3-6}$ spirocycloalkyl. In still another embodiment of the processes described herein, $R^2$ is halogen and m is 1.

In one preferred embodiment of the processes described herein, m is 0.

In one embodiment of the processes described herein, each $R^2$ is independently halogen or unsubstituted $C_{1-3}$ alkyl. In another embodiment of the processes described herein, $R^2$ is halogen or $C_{1-3}$ alkyl and m is 1.

In another embodiment of the processes described herein, each $R^2$ is independently unsubstituted $C_{1-3}$ haloalkyl, or unsubstituted $C_{1-3}$ alkoxy.

In one embodiment of the processes described herein, n is 1 or 2. In one preferred embodiment of the processes described herein, n is 3. In one such embodiment, n is 3 where each $R^{1a}$ and $R^{1b}$ is independently hydrogen, halogen, methyl, cyano, or cyclopropyl. In another such embodiment of the processes described herein, n is 3 where each $R^{1a}$ and $R^{1b}$ is independently hydrogen or halogen. In another such embodiment of the processes described herein, n is 3 where each $R^{1a}$ and $R^{1b}$ is independently hydrogen or methyl. In another such embodiment of the processes described herein, n is 3 where each $R^{1a}$ and $R^{1b}$ is independently hydrogen or cyclopropyl.

In one embodiment of the processes described herein, the compound of formula (II) prepared according to process P1, P2, P3, or P4 has formula:

(2a)

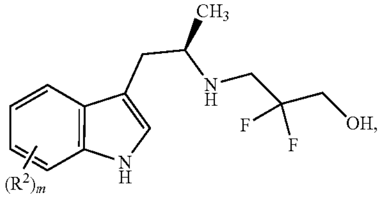

(2b)

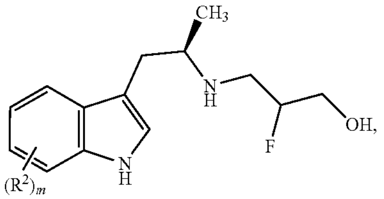

(2c)

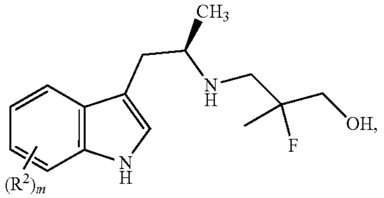

-continued (2d)

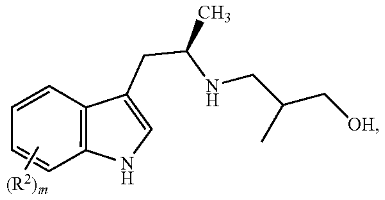

(2e)

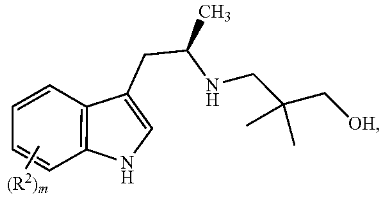

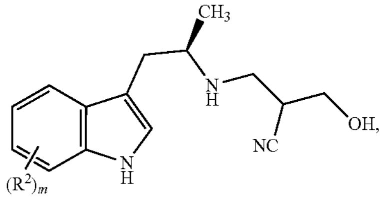

(2g)

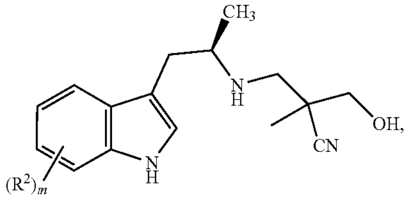

or

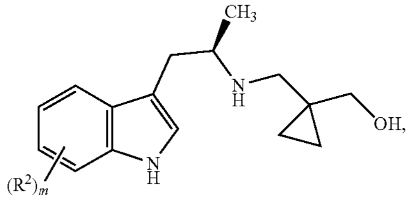

or a stereoisomer or salt thereof.

In one embodiment of the processes described herein, the compound of formula (II) or a stereoisomer or salt thereof prepared according to process P1, P2, P3, or P4 has formula (2), (2a), or (2b). In another embodiment of the processes described herein, the compound of formula (II) prepared according to process P1, P2, P3, or P4 has formula (2c) or (2d). In another embodiment of the processes described herein, the compound of formula (II) or a stereoisomer or salt thereof prepared according to process P1, P2, P3, or P4 has formula (2e) or (2f). In still another embodiment of the processes described herein, the compound of formula (II) or a stereoisomer or salt thereof prepared according to process P1, P2, P3, or P4 has formula (2g).

In one preferred embodiment of the processes described herein, the compound of formula (II) or a stereoisomer or salt thereof prepared according to process P1, P2, P3, or P4 has formula:

(2)

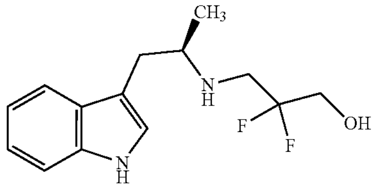

or a salt thereof.

In one embodiment, the compound of formula (2) is prepared according to the process P1 as described herein. In another embodiment, the compound of formula (2) is prepared according to the process P2 as described herein. In another embodiment, the compound of formula (2) is prepared according to the process P3 as described herein. In another embodiment, the compound of formula (2) is prepared according to the process P4 as described herein.

Further provided herein is a process (P5) for the preparation of a compound of formula (I):

(I)

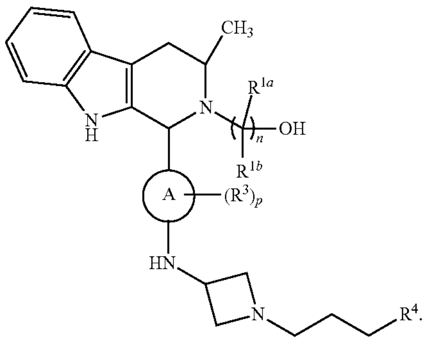

or a pharmaceutically acceptable salt thereof, wherein $R^{1a}$, $R^{1b}$, and n are as described herein, the process comprising contacting a compound of formula (II) or a stereoisomer or salt thereof prepared according to the process P1, P2, P3, or P4 as described herein or a salt thereof as described herein with a compound of formula (X):

(X)

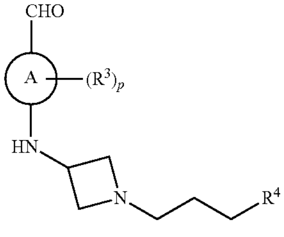

or a stereoisomer or salt thereof, wherein ring A is phenyl or pyridinyl;

each $R^3$ is independently hydrogen, halogen, or $C_{1-3}$ alkyl;

$R^4$ is halogen or —CN; and p is 1 or 2.

In one embodiment of the process (P5) described herein, the process further comprises the presence of tartaric acid.

In one embodiment of the process (P5) described herein, the compound of formula X has formula:

(10)

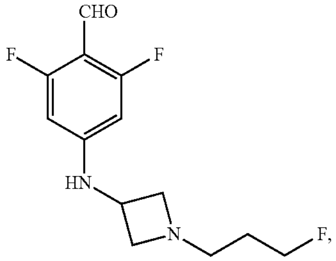

(10a)

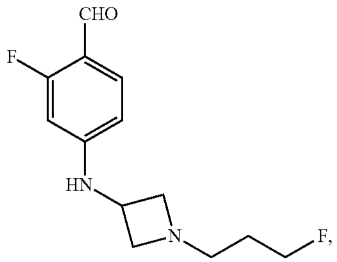

(10b)

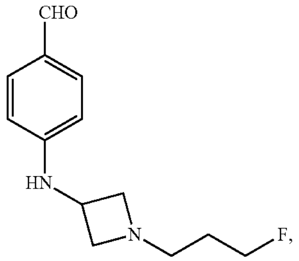

(10c)

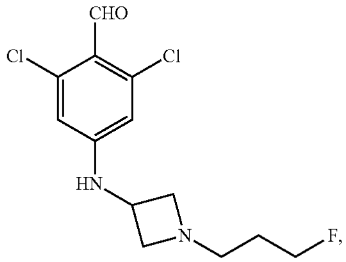

(10d)

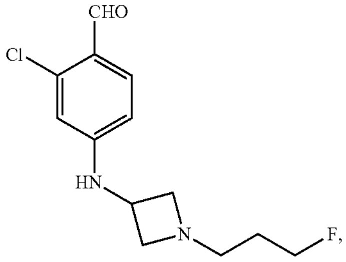

(10e)

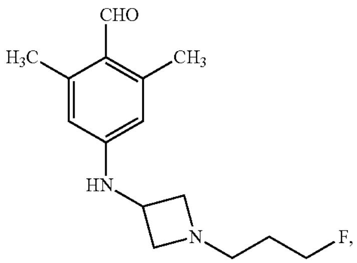

-continued
(10f)
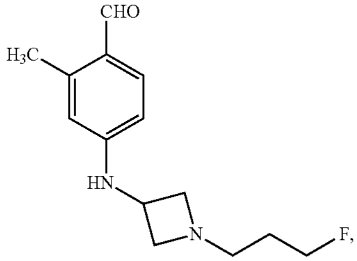
,
(10g)
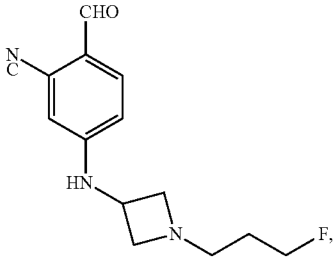
,
(10h)
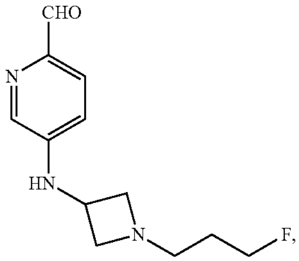
,
(10i)
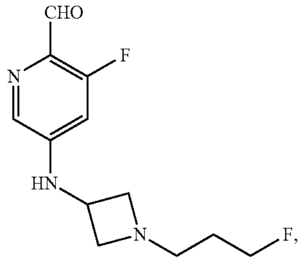
,
(10j)
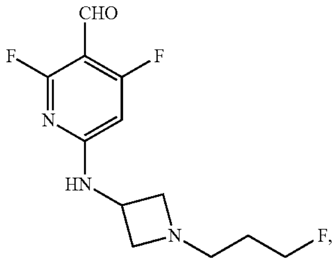
,
(10k)
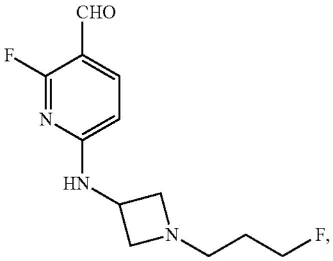
,
-continued
(10l)
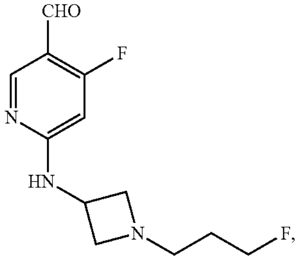
,
(10m)
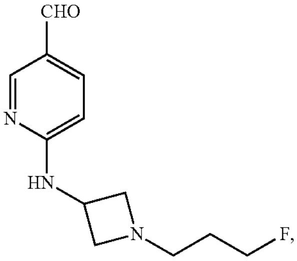
,
(10n)
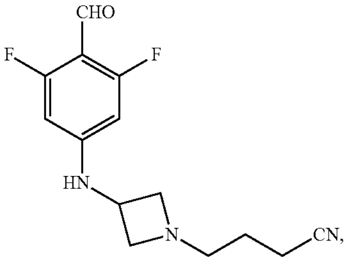
,
(10p)
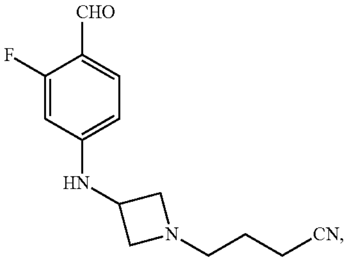
,
(10q)
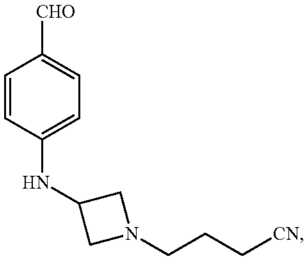
,
(10r)
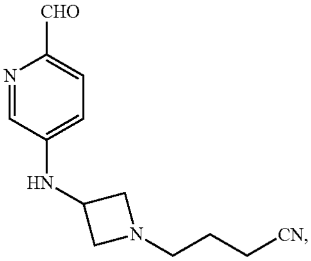
, -continued (10s)

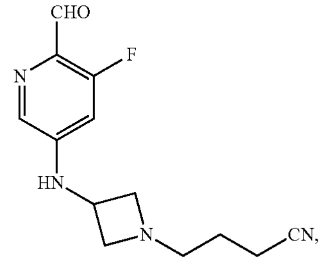

(10t)

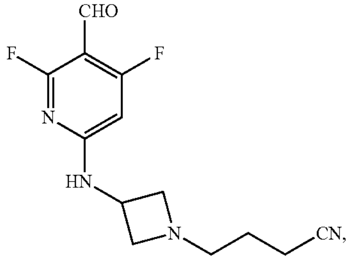

(10u)

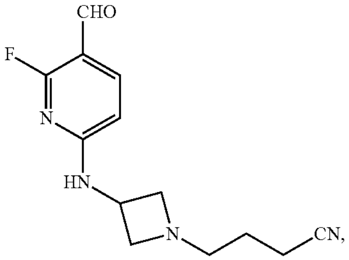

(10v)

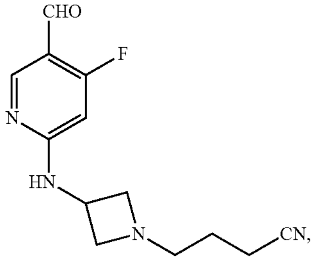

or (10w)

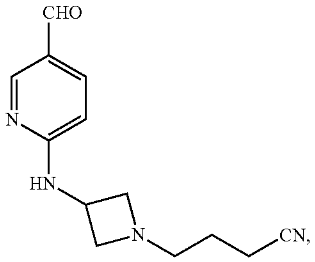

or a salt thereof.

In one such embodiment, the salt thereof is a tartrate salt.

In one embodiment of the process (P5) described herein, the compound of formula X or a salt thereof has formula (10), (10a), or (10b). In another embodiment of the process (P5) described herein, the compound of formula X or a salt thereof has formula (10c), (10d), or (10e). In another embodiment of the process (P5) described herein, the compound of formula X or a salt thereof has formula (10f)-(10m). In another embodiment of the process (P5) described herein, the compound of formula X or a salt thereof has formula (10n)-(10w).

In one embodiment of the process (P5) described herein, the compound of formula (I) has formula:

(1)

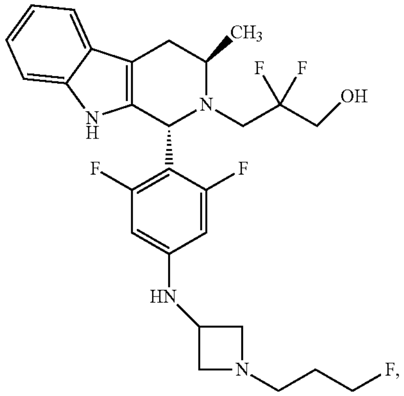

(1a)

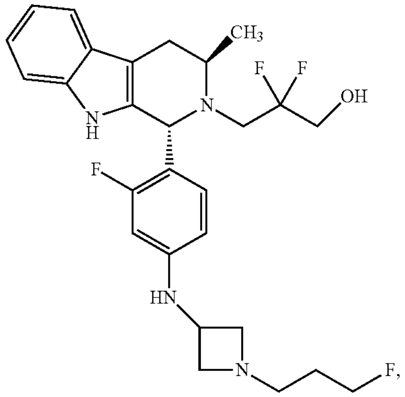

(1b)

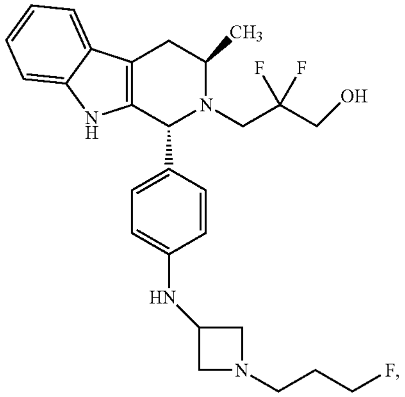

-continued
(1c)
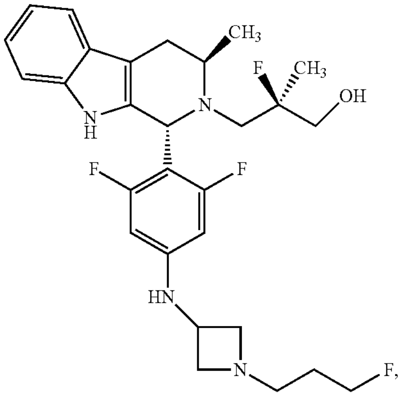
(1d)
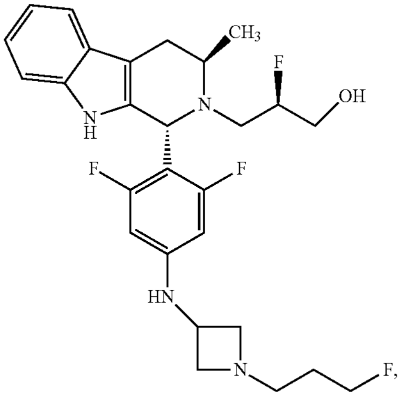
(1e)
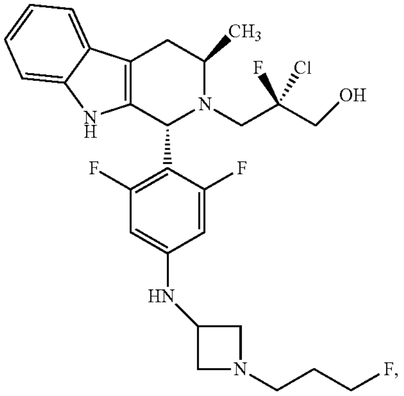
(1f)
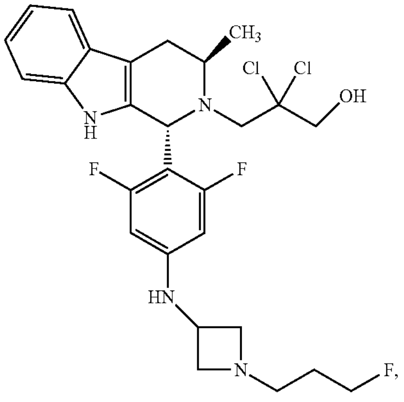
-continued
(1g)
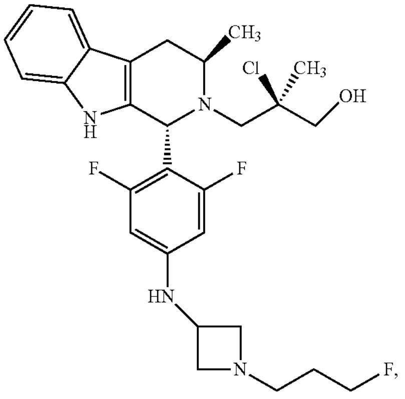
(1h)
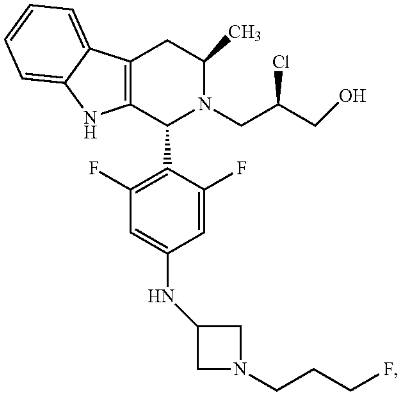
(1i)
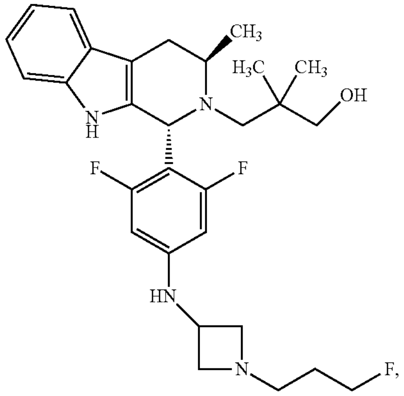
(1j)
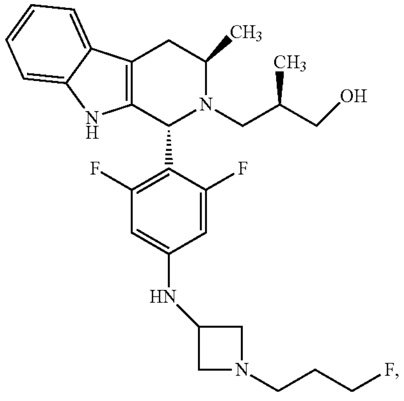

-continued
(1k)
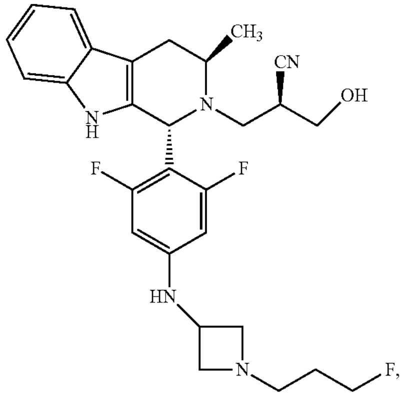
(1l)
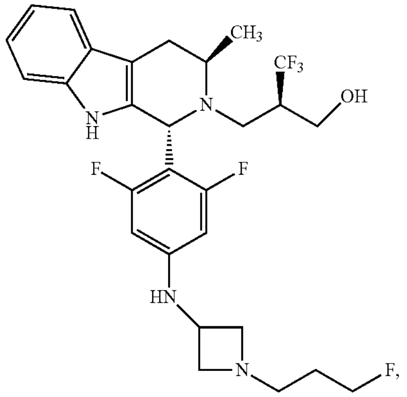
(1m)
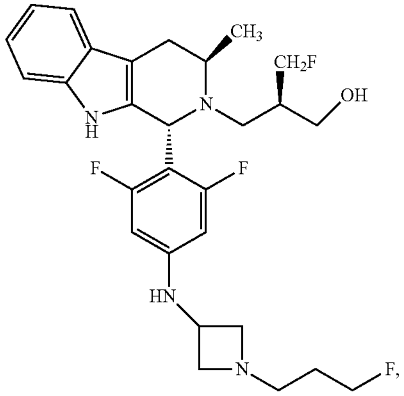
(1n)
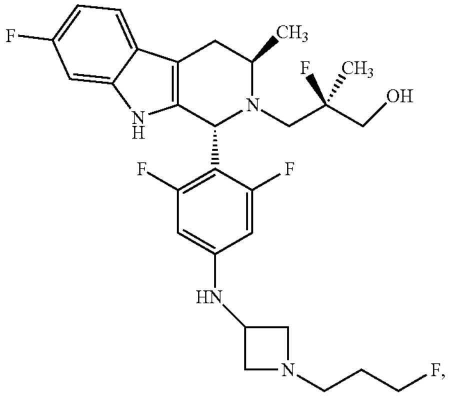
-continued
(1o)
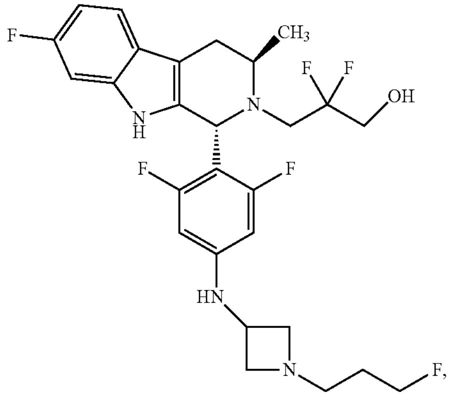
(1p)
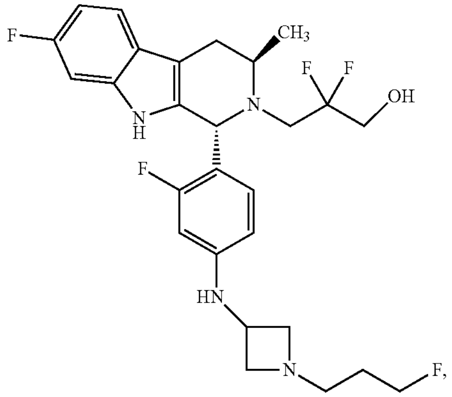
(1q)
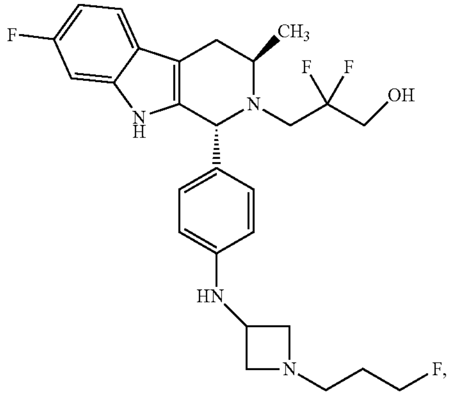
(1r)
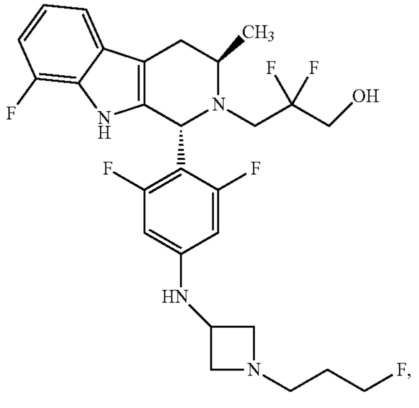

-continued
(1s)
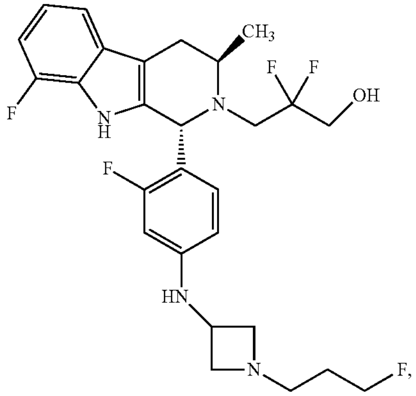
(1t)
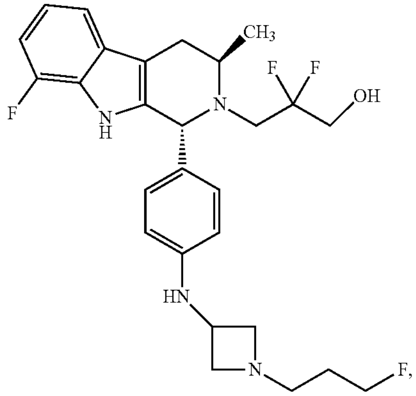
(1u)
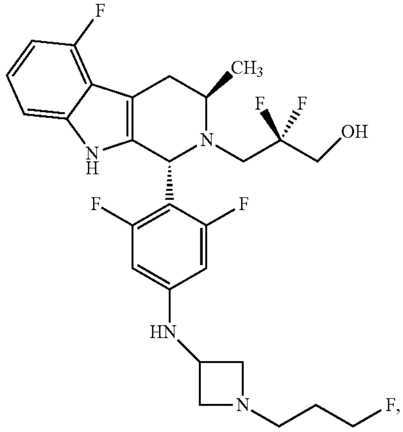
-continued
(1v)
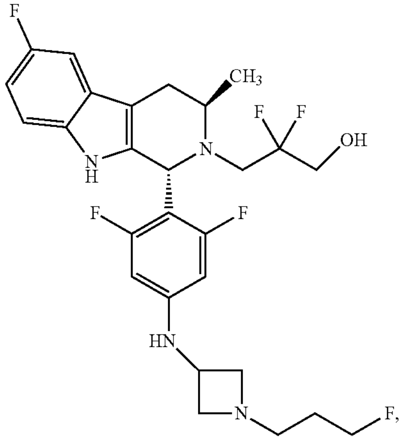
(1w)
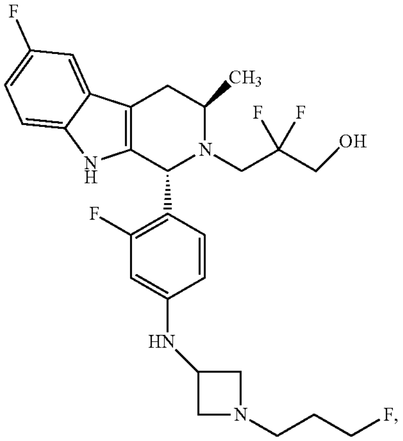
(1x)
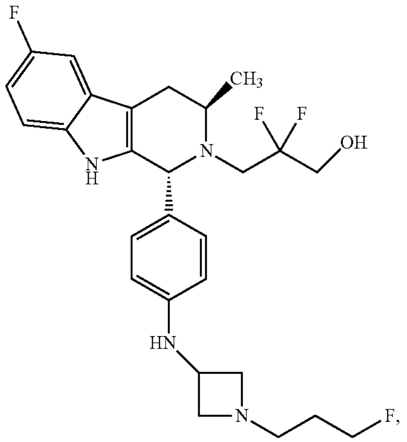
or -continued (1y)

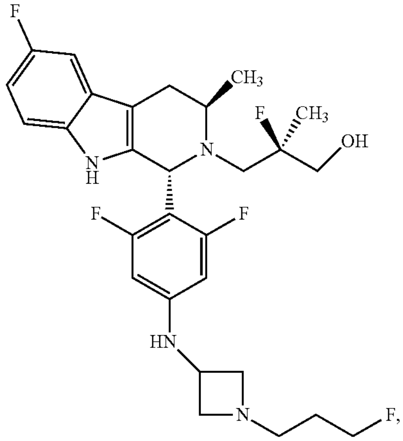

or a pharmaceutically acceptable salt thereof.

In one such embodiment, the pharmaceutically acceptable salt thereof is a tartrate salt.

In one embodiment of the process (P5) described herein, the compound of formula (I) or a pharmaceutically acceptable salt thereof has formula (1), (1a), (1 b), or (1d). In another embodiment of the process (P5) described herein, the compound of formula (I) or a pharmaceutically acceptable salt thereof has formula (1c), or (1e)-(1j). In another embodiment of the process (P5) described herein, the compound of formula (I) or a pharmaceutically acceptable salt thereof has formula (1k). In another embodiment of the process (P5) described herein, the compound of formula (I) or a pharmaceutically acceptable salt thereof has formula (11)-(1n). In another embodiment of the process (P5) described herein, the compound of formula (I) or a pharmaceutically acceptable salt thereof has formula (1o)-(1t). In another embodiment of the process (P5) described herein, the compound of formula (I) has or a pharmaceutically acceptable salt thereof formula (1u). In another embodiment of the process (P5) described herein, the compound of formula (I) or a pharmaceutically acceptable salt thereof has formula (1v)-(1y).

In one embodiment, the compound of formula (I) has formula:

(1)

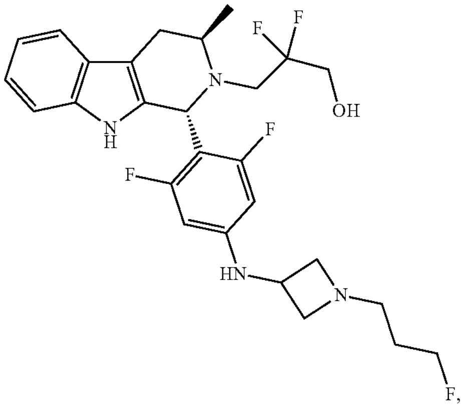

or a pharmaceutically acceptable salt thereof.

In another embodiment, the compound of formula (I) has formula:

(A)

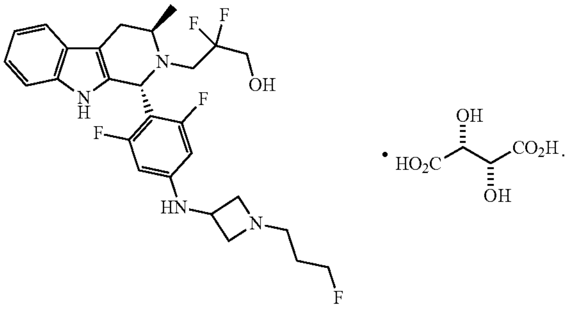

In another aspect provided herein is a process (P6) for the synthesis of a compound having the formula (1):

(1)

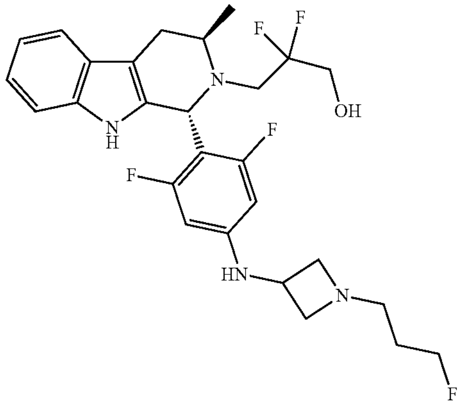

or a pharmaceutically acceptable salt thereof, the process comprising:

(a) contacting a compound of formula (2) or a salt thereof, (2)

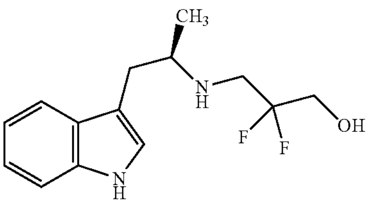

wherein the compound of formula (2) is synthesized according to process P1, P2, P3, or P4 as described herein;

(b) with a compound of formula (10) or a salt thereof, (10)

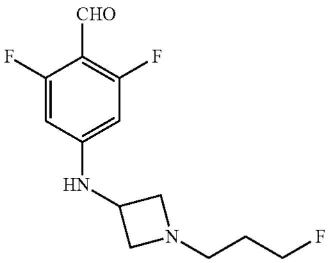

thereby making a compound of formula (1) or a pharmaceutically acceptable salt thereof.

In one preferred embodiment of the process (P6) described herein, the compound of formula (2) or salt thereof is prepared using process P2 or P3.

In another aspect provided herein is a process (P7) for the synthesis of a compound having the formula (A):

(A)

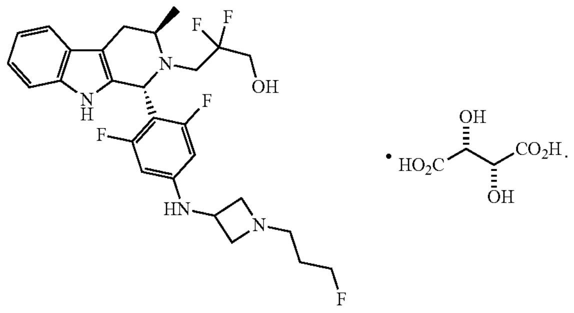

the process comprising:

(a) contacting a compound of formula (2), (2)

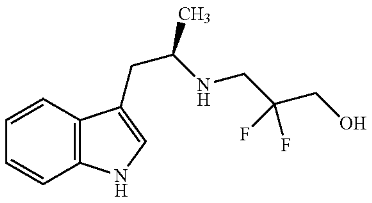

or a salt thereof, wherein the compound of formula (2) or salt thereof is synthesized according to process P1, P2, P3, or P4 as described herein;

(b) with a compound of formula (10) or a salt thereof in the presences of tartaric acid, (10)

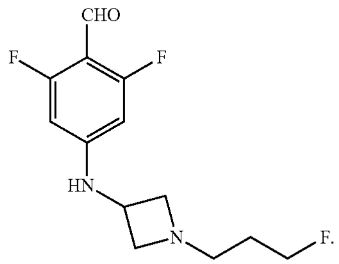

thereby making a compound of formula (A).

In one embodiment of the process (P7) described herein, step (b) includes EtOH. In one such embodiment, the reaction takes place at about 70° C.

In one embodiment of the process (P6) and (P7) described herein, the compound of formula (2) or salt thereof is prepared according to the process P1, P2, P3, or P4 as described herein. In one embodiment of the process (P6) and (P7) described herein, the compound of formula (2) or salt thereof is prepared according to the process P1, P2, P3, or P4 as described herein. In one embodiment of the process (P6) and (P7) described herein, the compound of formula (2) or salt thereof is prepared according to the process P2 or P3 as described herein. In one embodiment of the process (P6) and (P7) described herein, the compound of formula (2) or salt thereof is prepared according to the process P1 as described herein. In another embodiment of the process (P6) and (P7) described herein, the compound of formula (2) or salt thereof is prepared according to the process P2 as described herein. In another embodiment of the process (P6) and (P7) described herein, the compound of formula (2) or salt thereof is prepared according to the process P3 as described herein. In another embodiment of the process (P6) and (P7) described herein, the compound of formula (2) or salt thereof is prepared according to the process P4 as described herein.

In one embodiment of the process (P6) and (P7) described herein, the compound of formula (6) is prepared by:

(a) contacting a compound of formula (12a)

(12a)

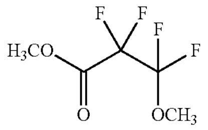

with $H_2SO_4$ to make a compound of formula (12b)

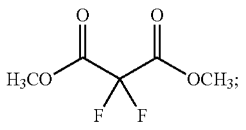

(b) reducing the compound of formula (12b) to make a compound of formula (12c)

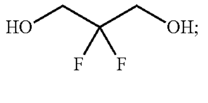

(c) cyclizing the compound of formula in the presence of $SOCl_2$ to make the compound of formula (12d)

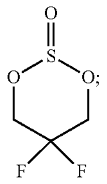

and (d) contacting the compound of formula (12d) with $FeCl_3$, NaOCl and a base, thereby making the compound of formula (6).

In one such embodiment, the base of step (d) is NaOH, KOH, or LiOH. In one such embodiment, the base of step (d) is NaOH. In one embodiment, step (d) is carried out in DCM and water.

In another embodiment of the process (P6) and (P7) described herein, the processes independently further comprise recrystallization according to Scheme A or B below:

Scheme A

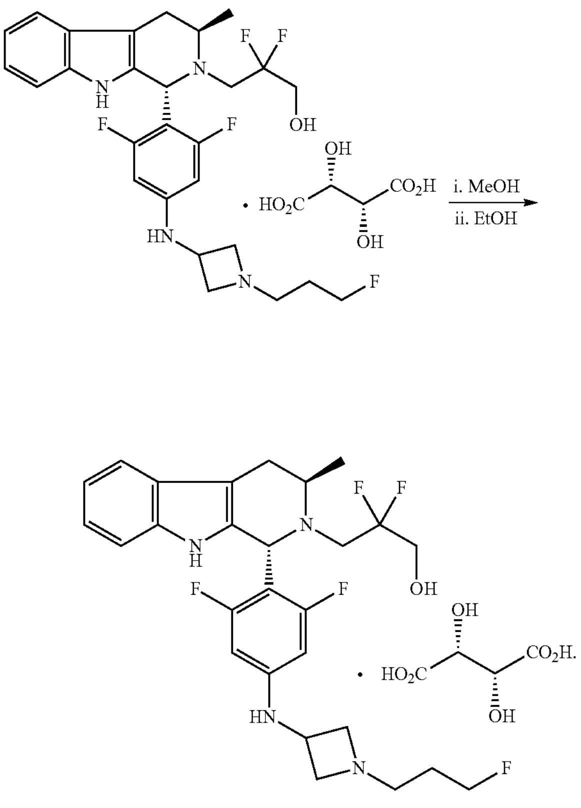

Scheme B

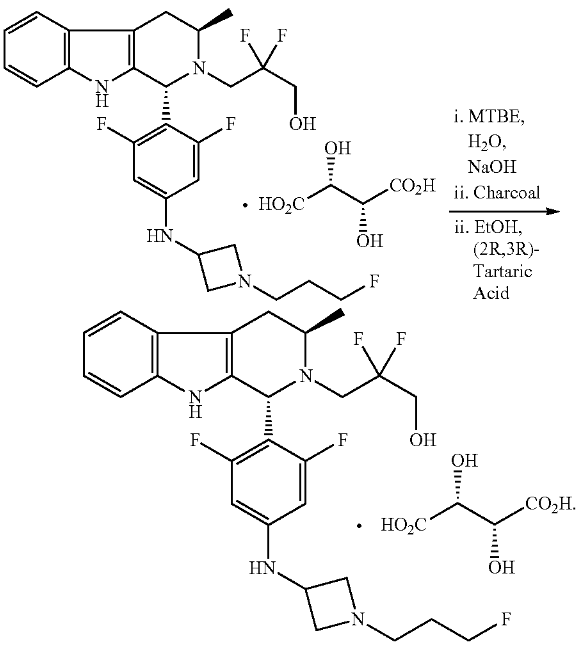

The compound of formula (I) and pharmaceutically acceptable salts thereof synthesized according to any of the processes described herein can be administered in an effective amount (e.g. an amount as described herein) for treating cancer.

In one aspect provided herein is a method of treating cancer by administering an effective amount of a compound of formula (I) or pharmaceutically acceptable salt thereof synthesized according to any of the processes described herein to a patient having cancer. In one embodiment, the compound is a compound of formula (1) or formula (A).

In another aspect provided herein is a method of treating lung cancer, ovarian cancer, endometrial cancer, prostate cancer, uterine cancer, or breast cancer by administering an effective amount of a compound of formula (I) or pharmaceutically acceptable salt thereof synthesized according to any of the processes described herein to a patient having said cancer. In one embodiment, the cancer is ovarian cancer or endometrial cancer. In one embodiment, the cancer is breast cancer.

Further provided herein are methods of treating breast cancer in a patient having breast cancer by administering an effective amount of a compound of formula (I) or pharmaceutically acceptable salt thereof synthesized according to any of the processes described herein. In one such embodiment, the compound is Compound (1) or Compound (A) as described herein.

The compound of formula (I) or pharmaceutically acceptable salt thereof synthesized according to any of the processes described herein can be used in the manufacture of a medicament for use in treating breast cancer as described herein.

The methods of treating breast cancer provided herein comprise treatment where the breast cancer can be hormone receptor positive breast cancer (e.g. ER+ breast cancer), HER2-positive breast cancer, HER2-negative breast cancer, or triple negative breast cancer (TNBC).

In one embodiment, the breast cancer is HER2-negative breast cancer. HER2-negative breast cancer can be defined herein as, for example, a HER2 IHC score of 0 or 1+, or an IHC score of 2+ accompanied by a negative fluorescence, chromogenic, or silver in situ hybridization test indicating the absence of HER2-gene amplification, or a HER2/CEP17 ratio of <2.0, or local clinical guidelines. In one embodiment, the breast cancer is ER+/HER2− breast cancer. The breast cancer can be stage 0, I, II, III, or IV as understood in the art.

In another embodiment, the breast cancer is locally advanced or metastatic breast cancer (mBC).

In one embodiment, the compound of formula (I) or pharmaceutically acceptable salt thereof synthesized according to any of the processes described herein can be administered as a component of adjuvant therapy. In another embodiment, the compound of formula (I) or pharmaceutically acceptable salt thereof synthesized according to any of the processes described herein can be administered as a component of neoadjuvant therapy.

Breast cancer patients described herein may be premenopausal before treatment with a compound or solid form as described herein. Breast cancer patients described herein may be postmenopausal before treatment with a compound or solid for as described herein.

The methods provided herein include administering an effective amount of a compound of formula (I) or pharmaceutically acceptable salt thereof synthesized according to any of the processes described herein to the patient at an amount as set forth herein. The effective amount can be, for example, an amount of about 10 mg, 30 mg, 50 mg, 90 mg, 100 mg, 125 mg, or 250 mg. In one embodiment of the methods provided herein, the compound of formula (I) or pharmaceutically acceptable salt thereof synthesized according to any of the processes described herein is administered orally. In one embodiment, the compound of formula (I) or pharmaceutically acceptable salt thereof synthesized according to any of the processes described herein is administered as a tablet (e.g. a coated or non-coated tablet). In another embodiment, the compound of formula (I) or pharmaceutically acceptable salt thereof synthesized according to any of the processes described herein is administered as a capsule. Thus, provided herein are compositions suitable for administration to a breast cancer patient where such compositions comprise an amount of a compound of formula (I) or pharmaceutically acceptable salt thereof synthesized according to any of the processes described herein of about 10 mg, 30 mg, 50 mg, 90 mg, 100 mg, 125 mg, or 250 mg in a tablet or capsule as set forth herein.

Systemic chemotherapy is considered as one standard of care (SOC) for patients with mBC, although no standard regimen or sequence exists. Patients of the methods described herein may have had previous treatment with one or more anti-cancer agents or radiation therapy. For example, in one embodiment, a patient may have been previously treated (e.g. with a 1L, 2L, 3L or more line therapy) with doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, ftutamide, nilutamide, bicalutamide, lapatinib, vinblastine, goserelin, leuprolide, pegfilgrastim, filgrastim, or venetoclax.

In another embodiment, a patient may have been previously treated (e.g. with a 1L, 2L, 3L or more line therapy) with an AKT inhibitor, a CDK4/6 inhibitor, a PARP inhibitor, or an aromatase inhibitor. In one embodiment, the AKT inhibitor is ipatasertib (GDC-0068). In one embodiment, the CDK4/6 inhibitor is abemaciclib, ribociclib, or palbociclib. In certain instances, a patient may have been previously treated with: (1) abemaciclib, ribociclib, or palbociclib; (2) ipatasertib; (3) everolimus or fulvestrant; (4) trastuzumab emtansine, trastuzumab, pertuzumab, or atezolizumab; or (5) alemtuzumab, bevacizumab, cetuximab, panitumumab, rituximab, tositumomab, or a combination thereof. Patients described herein may have had surgery prior to treatment with Compound (A) or the solid form thereof.

In one embodiment of the methods described herein, a patient described herein may have undergone surgical treatment such as, for example, surgery that is breast-conserving (i.e., a lumpectomy, which focuses on removing the primary tumor with a margin), or more extensive (i.e., mastectomy, which aims for complete removal of all of the breast tissue) prior to administration of a combination therapy described herein. In another embodiment, a patient described herein may undergo surgical treatment following treatment with a combination therapy described herein.

Radiation therapy is also administered post-surgery to the breast/chest wall and/or regional lymph nodes, with the goal of killing microscopic cancer cells left post-surgery. In the case of a breast conserving surgery, radiation is administered to the remaining breast tissue and sometimes to the regional lymph nodes (including axillary lymph nodes). In the case of a mastectomy, radiation may still be administered if factors that predict higher risk of local recurrence are present. In some embodiments of the methods provided herein a patient described herein may have received radiation therapy prior to administration of a combination therapy described herein. In other embodiments of the methods provided herein a patient described herein may have receive radiation therapy following administration of a combination therapy described herein.

In another embodiment, a patient herein may be refractory to one or more anti-cancer therapies. For example, a patient herein may be refractory to aromatase inhibitors. In another example, a patient herein may be refractory to a selective estrogen receptor degrader (SERD) such as, for example, fulvestrant. In still another example, a patient may be refractory to one or more endocrine therapies such as, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, or ospemifene. In another embodiment, a patient may be refractory to abemaciclib, anastrozole, exemestane, fulvestrant, goserelin, letrozole, leuprorelin, megestrol, palbociclib, tamoxifen, or toremifene. In another example, a patient may be refractory to treatment with trastuzumab emtansine, trastuzumab, pertuzumab, atezolizumab, pembrolizumab, durvalumab, avelumab, or nivolumab.

Also provided herein are methods of treating ER+, HER2− laBC or mBC in a patient having such a cancer. In one embodiment, the methods include treating ER+, HER2− laBC or mBC in a patient having such a cancer by administering to the patient a compound of formula (I) or pharmaceutically acceptable salt thereof synthesized according to any of the processes described herein over a 28-day cycle.

The compound of formula (I) or pharmaceutically acceptable salt thereof synthesized according to any of the processes described herein can also be used in methods comprising inhibiting ERalpha in a patient. Such methods comprise administering an amount of such a compound to the patient.

The compound of formula (I) or pharmaceutically acceptable salt thereof synthesized according to any of the processes described herein can be administered in combination with one or more anti-cancer agents. Administration "in combination" as set forth herein includes sequential administration (in any order) of a compound described herein and one or more anti-cancer therapies as well as simultaneous administration. Accordingly, provided herein are methods of treating breast cancer in a patient having breast cancer, such methods comprising administering compound of formula (I) or pharmaceutically acceptable salt thereof synthesized according to any of the processes described herein in combination with one or more additional anti-cancer therapies. In one embodiment, the anti-cancer therapy comprises doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, ftutamide, nilutamide, bicalutamide, lapatinib, vinblastine, goserelin, leuprolide, pegfilgrastim, filgrastim, or venetoclax.

In one embodiment provided herein is a method of treating breast cancer in a patient having breast cancer by administering an effective amount of compound of formula (I) or pharmaceutically acceptable salt thereof synthesized according to any of the processes described herein in combination with doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, ftutamide, nilutamide, bicalutamide, lapatinib, vinblastine, goserelin, leuprolide, pegfilgrastim, filgrastim, or venetoclax.

In another aspect provided herein is a method of treating breast cancer in a patient having breast cancer by administering an effective amount of compound of formula (I) or pharmaceutically acceptable salt thereof synthesized according to any of the processes described herein in combination with paclitaxel, albumin-bound paclitaxel, methotrexate, anastrozole, exemestane, toremifene, letrozole, tamoxifen, 4-hydroxy tamoxifen, raloxifene, droloxifene, trioxifene, keoxifene, or venetoclax. In still another aspect provided herein is a method of treating breast cancer in a patient having breast cancer by administering an effective amount of compound of formula (I) or pharmaceutically acceptable salt thereof synthesized according to any of the processes described herein in combination with fulvestrant, paclitaxel, albumin-bound paclitaxel, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, or ospemifene.

In still another aspect provided herein is a method of treating breast cancer in a patient having breast cancer by administering an effective amount of a compound of formula (I) or pharmaceutically acceptable salt thereof synthesized according to any of the processes described herein in combination with a CDK4/6 inhibitor, a PARP inhibitor, or an aromatase inhibitor.

In a further aspect provided herein is a method of treating breast cancer in a patient having breast cancer where the method comprises administering an effective amount of a compound of formula (I) or pharmaceutically acceptable salt thereof synthesized according to any of the processes described herein in combination with a CDK4/6 inhibitor where the CDK4/6 inhibitor is abemaciclib, ribociclib, or palbociclib. In one embodiment, the method comprises administering Compound (A) in combination with palbociclib. In still another embodiment, the method comprises administering Compound (A) in combination with abemaciclib or ribociclib. In another aspect provided herein is a kit comprising (i) a compound of formula (I) or pharmaceutically acceptable salt thereof synthesized according to any of the processes described herein; (ii) a CDK4/6 inhibitor (e.g. palbociclib) in a second unit dosage form; and a container containing each dosage form.

The dose of abemaciclib may be 50 mg to 500 mg daily, or 150 mg to 450 mg daily and the dosing can be daily in 28 day cycles or less than 28 days per 28 day cycles such as 21 days per 28 day cycle or 14 days per 28 day cycle or 7 days per 28 day cycles. In one embodiment, abemaciclib is dosed once daily or preferably on a bid schedule where dosing is oral. In the case of bid dosing, the doses can be separated by 4 hours. 8 hours or 12 hours. In certain embodiments. abemaciclib is dosed at 150 mg orally bid where each dose is administered about 12 hr apart. In certain embodiments, the dose of abemaciclib is administered in accordance with a package insert.

The dose of ribociclib may be 200 mg to 1,000 mg daily; or 250 mg to 750 mg daily and the dosuig can be daily in 28 day cycles or less than 28 days per 28 day cycles such as 21 days per 28 day cycle or 14 days per 28 day cycle or 7 days per 28 day cycles. In one embodiment, ribociclib is dosed once daily where dosing is oral. In certain embodiments, the dose of ribociclib is administered in accordance with a package insert.

The dose of palbociclib may be 25 mg to 250 mg daily or 50 mg to 125 mg daily or from 75 mg to 125 mg daily or 75 mg daily to 100 mg daily or 125 mg daily. The dosing can be daily in 28 day cycles or less than 28 days per 28 day cycles such as 21 days per 28 day cycle or 14 days per 28 day cycle or 7 days per 28 day cycles. In one embodiment, palbociclib is dosed once daily where dosing is oral. In certain embodiments, the dose of palbociclib is administered in accordance with a package insert.

Further provided herein is a method of treating ER+, HER2− IaBC or mBC in a patient having such a cancer where the method comprises administering to the patient a combination therapy comprising a compound of formula (I) or pharmaceutically acceptable salt thereof synthesized according to any of the processes described herein and palbociclib, wherein said combination therapy is administered over one or more 28-day cycles.

Still further provided herein is a method of treating ER+, HER2− IaBC or mBC in a patient having such a cancer where the method comprises administering to the patient a combination therapy described herein comprising a dosing regimen comprising: (i) administering a compound of formula (I) or pharmaceutically acceptable salt thereof synthesized according to any of the processes described herein QD on days 1-28 of a first 28-day cycle; and (ii) administering palbociclib QD on days 1-21 of the first 28-day cycle.

In one such embodiment, a compound of formula (I) or pharmaceutically acceptable salt thereof synthesized according to any of the processes described herein is administered as a fixed dose or QD administration. In another such embodiment, the administration is oral (PO), where compound of formula (I) or pharmaceutically acceptable salt thereof synthesized according to any of the processes described herein is formulated as a tablet or capsule. In another such embodiment, such a compound is administered at an amount of about 1 mg-100 mg, 1 mg-50 mg, 1 mg-30 mg, 10 mg-100 mg, 10 mg-50 mg, or QD. In another such embodiment, such a compound is administered at an amount of about 10, 30, 50, or 100 mg. In still another such embodiment, palbociclib is administered according to a package insert. In a preferred embodiment, palbociclib is administered at an amount of 125 mg.

The methods of treating breast cancer as provided herein can include administration of the combination therapy described herein as part of a dosing regimen. In one embodiment, the dosing regimen comprises one or more cycles. In another embodiment, the dosing regimen comprises at least 2 cycles. In another aspect provided herein is the dosing regimen comprises 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 cycles. In still another embodiment, dosing regimen comprises about 2-72, 2-66, 2-60, 2-54, 2-48, 2-42, 2-36, 2-2-24, 2-18, or 2-12 cycles.

In another aspect provided herein the methods described herein comprise administering an effective amount of compound of formula (I) or pharmaceutically acceptable salt thereof synthesized according to any of the processes described herein in combination with an aromatase inhibitor (Al), where the Al is letrozole, anastrozole, exemestane, or testolactone.

In yet another aspect provided herein is a method of treating breast cancer in a patient having breast cancer by administering an effective amount of compound of formula (I) or pharmaceutically acceptable salt thereof synthesized according to any of the processes described herein in combination with a cancer immunotherapy (e.g. an antibody). In one embodiment, In one embodiment, a compound of formula (I) or pharmaceutically acceptable salt thereof synthesized according to any of the processes described herein is administered in combination with trastuzumab emtansine, trastuzumab, pertuzumab, atezolizumab, pembrolizumab, durvalumab, avelumab, or nivolumab, or a combination thereof. In one embodiment, a compound of formula (I) or pharmaceutically acceptable salt thereof synthesized according to any of the processes described herein is administered in combination with a cancer immunotherapy comprising PD-1 or PD-L1 inhibitor, where the cancer immunotherapy is atezolizumab, pembrolizumab, or nivolumab.

Also provided herein are methods of inhibiting tumor growth or producing tumor regression in a patient described herein by administering a compound of formula (I) or pharmaceutically acceptable salt thereof synthesized according to any of the processes described herein. In one such embodiment, the method includes administering a second agent such as palbociclib.

In one embodiment provided herein is a method of producing or improving tumor regression in a patient having mBC described herein by administering a compound of formula (I) or pharmaceutically acceptable salt thereof synthesized according to any of the processes described herein. In one such embodiment, the method includes administering a second agent such as palbociclib.

Pharmaceutical Formulations

The compound of formula (I) or pharmaceutically acceptable salt thereof synthesized according to any of the processes described herein can be administered, for example, orally, intramuscularly, subcutaneously, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. Compounds of formula (I) or pharmaceutically acceptable salt thereof synthesized according to any of the processes described herein can be formulated in pharmaceutical compositions as provided herein suitable for oral administration. In another embodiment, a compound of formula (I) or pharmaceutically acceptable salt thereof synthesized according to any of the processes described herein can be administered intramuscularly. In one preferred embodiment, the compound is Compound (A).

In one embodiment, compounds of formula (I) or pharmaceutically acceptable salt thereof synthesized according to any of the processes described herein are administered as pharmaceutical compositions capable of being administered to a subject orally or parenterally. Pharmaceutical compositions of the compound of formula (I) or pharmaceutically acceptable salt thereof synthesized according to any of the processes described herein can be prepared as oral dosage forms such as, for example, capsules, microcapsules, tablets (coated and non-coated tablets), granules, powders, pills, or suppositories. The compound of formula (I) or pharmaceutically acceptable salt thereof synthesized according to any of the processes described herein can be formulated for topical or parenteral use where the compound is dissolved or otherwise suspended in a solution suitable for injections, suspensions, syrups, creams, ointments, gels, sprays, solutions and emulsions. In one preferred embodiment, the compound is Compound (A).

Pharmaceutical compositions described herein include one or more pharmaceutically acceptable excipients such as, but not limited to: sucrose, starch, mannitol, sorbitol, lactose, glucose, cellulose, talc, calcium phosphate or calcium carbonate, cellulose, methylcellulose, hydroxymethylcellulose, hydroxypropylcellulose, carboxymethylcellulose, hydroxypropylstarch, polypropylpyrrolidone, polyvinylpyrrolidone, gelatin, gum arabic, polyethyleneglycol (PEG), starch, sodium bicarbonate, calcium citrate, magnesium stearate, sodium lauryl sulfate, sodium benzoate, sodium bisulfite, methylparaben, propylparaben, citric acid, sodium citrate or acetic acid, polyvinyl pyrroliclone, aluminum stearate), water, and cocoa butter. Uses as, for example, diluents, binders, lubricants and disintegrators of such excipients is well known in the art.

The pharmaceutical compositions described herein include an effective amount of the compound of formula (I) or pharmaceutically acceptable salt thereof synthesized according to any of the processes described herein. The dose of the compound (e.g. Compound (A)) described herein can be a measure of a specific amount of the compound (e.g. a standard dose amount) or can be measured as a function of, for example, a patient's body weight. In one embodiment, a compound described herein is administered in an amount equivalent to about 0.1, 0.5, 0.75, 1, 2, 3, 4, 5, 10, 15, 20, 30, 50, 75, 100, 200, or 250 mg/kg. In another embodiment, a compound of formula (I) (e.g. Compound (A)) or pharmaceutically acceptable salt thereof synthesized according to any of the processes described herein is administered in an amount of about 0.1 mg/kg to about 1 mg/kg; about 0.5 mg/kg to about 2 mg/kg; about 1 mg/kg to about 5 mg/kg; about 3 mg/kg to about 10 mg/kg; about 8 mg/kg to about 15 mg/kg; or about 15 mg/kg to about 30 mg/kg. In still another embodiment, a compound of formula (I) or pharmaceutically acceptable salt thereof synthesized according to any of the processes described herein is administered in an amount less than about 100 mg/kg, less than about 50 mg/kg, less than about 30 mg/kg, less than about 10 mg/kg, or less than about 1 mg/kg.

In one embodiment, a compound of formula (I) or pharmaceutically acceptable salt thereof (e.g. Compound (A)) synthesized according to any of the processes described herein is administered at an amount of about 1, 5, 10, 20, 25, 30, 50, 60, 75, 90, 100, 120, 150, or 250 mg. In another embodiment, a compound of formula (I) or pharmaceutically acceptable salt thereof (e.g. Compound (A)) synthesized according to any of the processes described herein is administered in an amount of about 10 mg. In still another embodiment, a compound of formula (I) or pharmaceutically acceptable salt thereof (e.g. Compound (A)) synthesized according to any of the processes described herein is administered in an amount of about 30 mg. In still another embodiment, a compound of formula (I) or pharmaceutically acceptable salt thereof (e.g. Compound (A)) synthesized according to any of the processes described herein is administered in an amount of about mg. In one embodiment, the pharmaceutical composition comprising the compound of formula (I) or pharmaceutically acceptable salt thereof (e.g. Compound (A)) synthesized according to any of the processes described herein is administered in an amount prescribed above once per day (QD).

In another embodiment, a compound of formula (I) or pharmaceutically acceptable salt thereof (e.g. Compound (A)) synthesized according to any of the processes described herein is administered at an amount of about 1 mg to about 10 mg; about 10 mg to about 30 mg; about 10 mg to about 90 mg; about 30 mg to about 90 mg; or about 90 mg to about 250 mg. In one embodiment, the compound of formula (I) or pharmaceutically acceptable salt thereof (e.g. Compound (A)) synthesized according to any of the processes described herein at an amount of about 1, 10, 30, 50, 90, 100, or 150 mg. The doses of a compound of formula (I) or pharmaceutically acceptable salt thereof (e.g. Compound (A)) synthesized according to any of the processes described herein can be provided as a single dose (e.g. a single tablet or capsule of the given dosage amount) or can be provided as multiple doses given over a period of time (e.g. 2 or more tablets or capsules equating to the dosage amount). In one embodiment, the compound is Compound (1) or Compound (A).

Pharmaceutical compositions described herein can be administered once daily (QD); twice daily (BID), thrice daily (TID), every other day (Q2D), every three days (Q3D), or once a week. Further, doses of pharmaceutical compositions provided herein comprising a compound of formula (I) or pharmaceutically acceptable salt thereof (e.g. Compound (A)) synthesized according to any of the processes described herein can be administered before food (ac), after food (pc), or with food. In one embodiment, a compound of formula (I) or pharmaceutically acceptable salt thereof (e.g. Compound (A)) synthesized according to any of the processes described herein is administered QD for a treatment period (a period of time where the drug is administered to a patient described herein) followed by a rest period (a period of time where the drug is not administered to a patient described herein). Rest periods may include administration of anti-cancer agents other than a compound described herein. In one embodiment, a compound of formula (I) or pharmaceutically acceptable salt thereof (e.g. Compound (A)) synthesized according to any of the processes described herein is formulated for oral administration as provided herein and is administered QD for 20-28 days followed by a 3-10 day rest period. In another embodiment, the compound of formula (I) or pharmaceutically acceptable salt thereof (e.g. Compound (A)) synthesized according to any of the processes described herein is administered QD with no rest period.

Preferably a compound of formula (I) or pharmaceutically acceptable salt thereof (e.g. Compound (A)) synthesized according to any of the processes described herein is formulated for oral administration. Oral administration can promote patient compliance in taking the compound (e.g. formulated as a pharmaceutical composition), thereby increasing compliance and efficacy. Oral pharmaceutical compositions comprising a compound of formula (I) or pharmaceutically acceptable salt thereof (e.g. Compound (A)) synthesized according to any of the processes described herein include, but are not limited to, tablets (e.g. coated, non-coated and chewable) and capsules (e.g. hard gelatin capsules, soft gelatin capsules, enteric coated capsules, and sustained release capsules). Tablets can be prepared by direct compression, by wet granulation, or by dry granulation. Oral pharmaceutical compositions comprising a compound of formula (I) or pharmaceutically acceptable salt thereof (e.g. Compound (A)) synthesized according to any of the processes described herein can be formulated as understood in the art for delayed or prolonged release.

EMBODIMENTS

Provided below are exemplary embodiments of the invention described herein.

Embodiment No 1. A process for the preparation of a compound of formula (II):

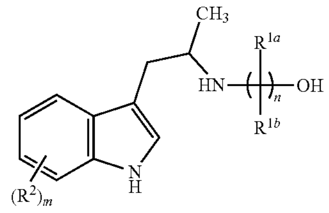

(II)

or a stereoisomer or salt thereof;

each of $R^{1a}$ and $R^{1b}$ is independently hydrogen, halogen, unsubstituted $C_{1-3}$ alkyl, unsubstituted $C_{1-3}$ haloalkyl, unsubstituted $C_{1-3}$ alkoxy, —CN, unsubstituted $C_{3-6}$ cycloalkyl, or unsubstituted $C_{3-6}$ spirocycloalkyl;

each $R^2$ is independently halogen, hydroxyl, —CN, unsubstituted $C_{1-3}$ alkyl, unsubstituted $C_{1-3}$ haloalkyl, or unsubstituted $C_{1-3}$ alkoxy;

m is 0, 1 or 2; and n is 1, 2, or 3;

the process comprising:

(a) contacting a compound of formula (III) or a stereoisomer or salt thereof, (III)

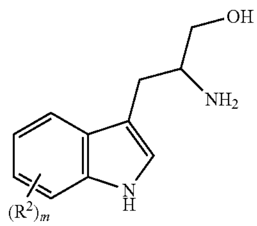

with a sulfonic acid to form a compound of formula (IIIa) or a stereoisomer or salt thereof;

(IIIa)

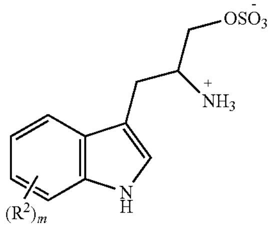

(b) contacting the compound of formula (IIIa) or a stereoisomer or salt thereof with a base to form compound of formula (IV) or a stereoisomer or salt thereof;

(IV)

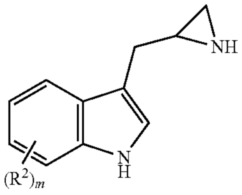

(c) hydrogenating the compound of formula (IV) or a stereoisomer or salt thereof to form a compound of formula (V) or a stereoisomer or salt thereof; and (V)

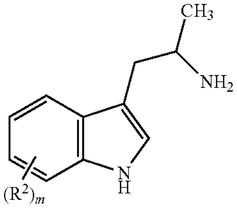

(d) contacting the compound of formula (V) or a stereoisomer or salt thereof with a compound of formula (VI);

(VI)

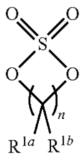

thereby forming a compound of formula (II) or a stereoisomer or salt thereof.

Embodiment 1a. The process of embodiment 1, wherein the compound of formula (III) is a compound of formula (III*).

Embodiment 1b. The process of embodiment 1 or 1a, wherein the compound of formula (III*) is a compound of formula (3*, 3x*, 3y*, or 3z*).

Embodiment No 2. The process of embodiment 1, 1a, or 1 b, wherein the sulfonic acid is $H_2SO_4$ or $ClSO_3H$.

Embodiment No 3. The process of embodiment 1, 1a, or 1 b, wherein the base is a hydroxide base.

Embodiment No 4. The process of embodiment 3, wherein the base is KOH, NaOH, or LiOH.

Embodiment No 5. The process of any one of embodiments 1-4, wherein the hydrogenation is performed using a catalyst comprising Pd, Pt, or Ni.

Embodiment No 6. The process of embodiment 5, wherein the catalyst is Pd/C, Pt/C, or Raney Ni.

Embodiment No 7. The process of any one of embodiments 1-4, wherein the hydrogenation is performed using catalytic transfer hydrogenation in the presence of isopropanol, formic acid, formate, or ammonium.

Embodiment No 8. A process for the preparation of a compound of formula (II):

(II)

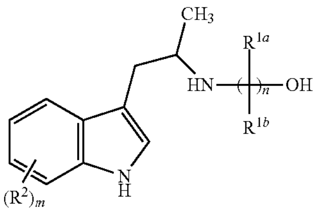

or a stereoisomer or salt thereof;

each of $R^{1a}$ and $R^{1b}$ is independently hydrogen, halogen, unsubstituted $C_{1-3}$ alkyl, unsubstituted $C_{1-3}$ haloalkyl, unsubstituted $C_{1-3}$ alkoxy, —CN, unsubstituted $C_{3-6}$ cycloalkyl, or unsubstituted $C_{3-6}$ spirocycloalkyl;

each $R^2$ is independently halogen, hydroxyl, —CN, $C_{1-3}$ alkyl, or $C_{1-3}$ haloalkyl, $C_{1-3}$ alkoxy;

m is 0, 1 or 2; and n is 1, 2 or 3;

the process comprising:

(a) contacting a compound of formula (VII), (VII)

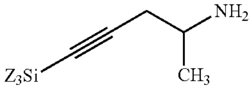

or a stereoisomer or salt thereof, wherein each Z is independently $C_{1-3}$ alkyl or phenyl, with a compound of formula (VI), (VI)

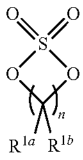

wherein $R^{1a}$ and $R^{1b}$ are as described herein, thereby synthesizing a compound of formula (VIIa);

(VIIa)

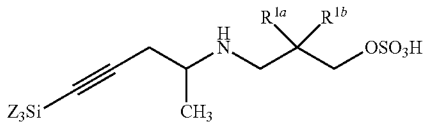

or a stereoisomer or salt thereof (b) contacting a compound of formula (VIIa) or a stereoisomer or salt thereof with an acid thereby synthesizing a compound of formula (VIIb);

(VIIb)

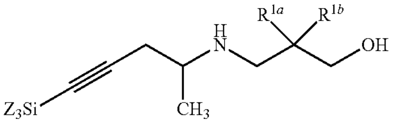

or a stereoisomer or salt thereof (c) contacting the compound of formula (VIIb) or a stereoisomer or salt thereof with 1,1'-carbonyldiimidazole thereby synthesizing a compound of formula (VIIc);

(VIIc)

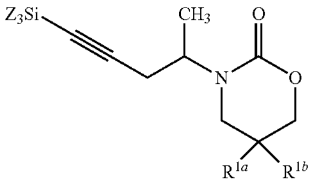

or a stereoisomer or salt thereof (d) contacting the compound of formula (VIIc) or a stereoisomer or salt thereof with a compound of formula (VIII) or a stereoisomer or salt thereof;

(VIII)

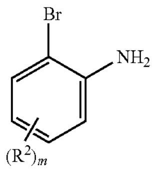

to make a compound of formula (Va) or a stereoisomer or salt thereof; and (Va)

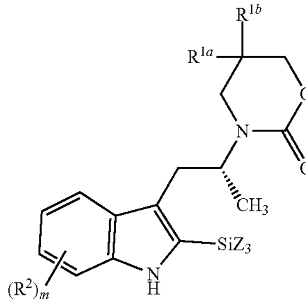

(e) contacting the compound of formula (Va) or a stereoisomer or salt thereof with a base followed by an acid thereby making the compound of formula (II) or a stereoisomer or salt thereof.

Embodiment No 9. A process for the preparation of a compound of formula (II):

(II)

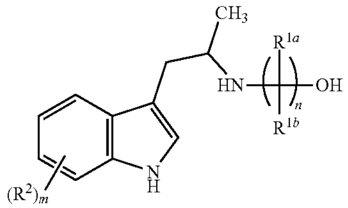

or a stereoisomer or salt thereof each of $R^{1a}$ and $R^{1b}$ is independently hydrogen, halogen, unsubstituted $C_{1-3}$ alkyl, unsubstituted $C_{1-3}$ haloalkyl, unsubstituted $C_{1-3}$ alkoxy, —CN, unsubstituted $C_{3-6}$ cycloalkyl, or unsubstituted $C_{3-6}$ spirocycloalkyl;

each $R^2$ is independently halogen, hydroxyl, —CN, $C_{1-3}$ alkyl, or $C_{1-3}$ haloalkyl, $C_{1-3}$ alkoxy;

m is 0, 1 or 2; and n is 1, 2 or 3;

the process comprising contacting a compound of formula (V);

(V)

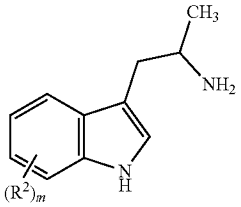

or a stereoisomer or salt thereof, with a compound of formula (VI), (VI)

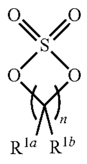

or a stereoisomer or salt thereof, wherein the compound of formula (V) is prepared by:

(a) contacting a compound of formula (VIIp)

(VIIp)

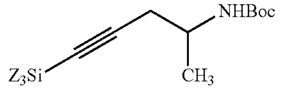

or a stereoisomer or salt thereof, wherein each Z is independently $C_{1-3}$ alkyl or phenyl, with a compound of formula (XII), (VIII)

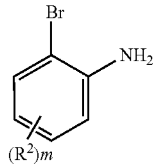

or a salt thereof, to make a compound of formula (Vb); and (Vb)

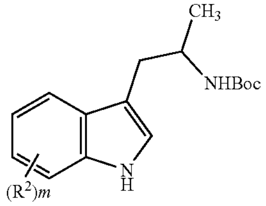

or a stereoisomer or salt thereof (b) contacting the compound of formula (Vb) or a stereoisomer or salt thereof with an acid thereby making the compound of formula (V) or a stereoisomer or salt thereof.

Embodiment No 10. The process of embodiment 8 or 9, wherein each Z is independently $C_{1-4}$ alkyl.

Embodiment No 11. The process of embodiment 8 or 9, wherein each Z is methyl, each Z is ethyl, each Z is isopropyl or wherein $SiZ_3$ is $Si(PhMe_2)$ or $Si(t\text{-}BuMe_2)$.

Embodiment No 12. The process of embodiment 8 or 9, wherein each Z is ethyl.

Embodiment No 13. The process of any one of embodiments 1-12, wherein the compound of formula (VI) is:

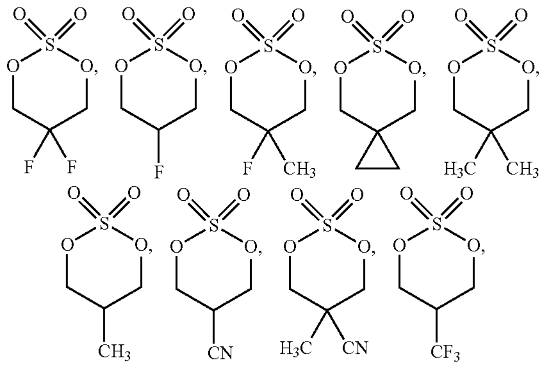

-continued

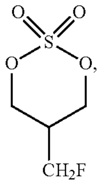

or

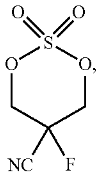

including stereoisomers thereof.

Embodiment No 14. A process for the preparation of a compound of formula (II):

(II)

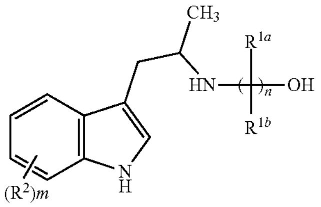

or a stereoisomer or salt thereof each of $R^{1a}$ and $R^{1b}$ is independently hydrogen, halogen, unsubstituted $C_{1-3}$ alkyl, unsubstituted $C_{1-3}$ haloalkyl, unsubstituted $C_{1-3}$ alkoxy, —CN, unsubstituted $C_{3-6}$ cycloalkyl, or unsubstituted $C_{3-6}$ spirocycloalkyl;

each $R^2$ is independently halogen, hydroxyl, —CN, $C_{1-3}$ alkyl, or $C_{1-3}$ haloalkyl, $C_{1-3}$ alkoxy;

m is 0, 1 or 2;

n is 1, 2 or 3;

the process comprising (a) contacting alanine with a compound of formula (IX), (IX)

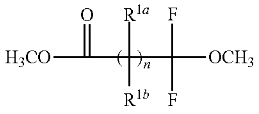

or a stereoisomer or salt thereof, to form a compound of formula (XI);

(XI)

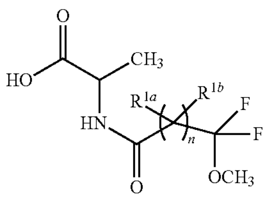

or a stereoisomer or salt thereof (b) contacting the compound of formula (XI) or a stereoisomer or salt thereof with a chlorinating agent, a compound of formula

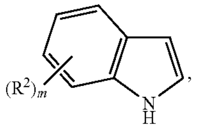

and an organoaluminum compound to form a compound of formula (Vc); and (Vc)

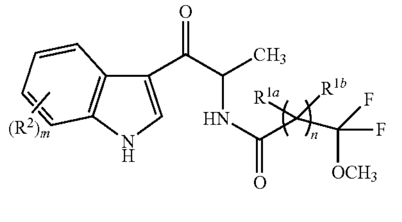

or a stereoisomer or salt thereof (c) contacting the compound of formula (Vc) or a stereoisomer or salt thereof with a reducing agent thereby forming a compound of formula (II) or a stereoisomer or salt thereof.

Embodiment No 15. The process of embodiment 14, wherein the organoaluminum compound has the formula X 3 A1, where X is independently Cl or $C_{1-4}$ alkyl.

Embodiment No 16. The process of embodiment 14, wherein X is independently methyl, ethyl, n-propyl, isopropyl, n-butyl, or isobutyl.

Embodiment No 17. The process of any one of embodiments 14-16, wherein the organoaluminum compound is trimethyl aluminum, triethyl aluminum, triisobutyl aluminum, dimethyl aluminum chloride, diethyl aluminum chloride, or ethyl aluminum dichloride.

Embodiment No 18. The process of any one of embodiments 14-17, wherein the organoaluminum compound is trimethyl aluminum.

Embodiment No 19. The process of any one of embodiments 14-18, wherein the reducing agent is sodium aluminum hydride.

Embodiment No 20. The process of any one of embodiments 14-19, wherein the chlorinating agent is $SOCl_2$, methyl chloroformate, ethyl chloroformate, isobutyl chloroformate, pivaloyl chloride, or oxalyl chloride.

Embodiment No 21. The process of embodiment 20, wherein the chlorinating agent is oxalyl chloride.

Embodiment No 22. The process of embodiment 21, wherein the chlorinating agent is in the presence of N-formyl pyrrolidine or N,N-dimethylformamide.

Embodiment No 23. The process of any one of embodiments 1-22, wherein $R^{1a}$ and $R^{1b}$ are independently hydrogen, halogen, cyano, unsubstituted $C_{1-3}$ alkyl, or cyclopropyl.

Embodiment No 24. The process of any one of embodiments 1-22, wherein $R^{1a}$ and $R^{1b}$ are independently hydrogen, halogen, or methyl.

Embodiment No 25. The process of any one of embodiments 1-22, wherein $R^{1a}$ is hydrogen and $R^{1b}$ is halogen, methyl, cyano, or cyclopropyl.

Embodiment No 26. The process of any one of embodiments 1-22, wherein $R^{1a}$ is hydrogen and $R^{1b}$ is halogen.

Embodiment No 27. The process of any one of embodiments 1-22, wherein $R^{1a}$ is hydrogen and $R^{1b}$ is methyl.

Embodiment No 28. The process of any one of embodiments 1-22, wherein $R^{1a}$ is methyl and $R^{1b}$ is halogen, methyl, cyano, or cyclopropyl.

Embodiment No 29. The process of any one of embodiments 1-22, wherein $R^{1a}$ is halogen and $R^{1b}$ is halogen, methyl, cyano, or cyclopropyl.

Embodiment No 30. The process of any one of embodiments 1-22, wherein $R^{1a}$ and $R^{1b}$ are independently halogen, or methyl.

Embodiment No 31. The process of any one of embodiments 1-22, wherein $R^{1a}$ is halogen and $R^{1b}$ is methyl.

Embodiment No 32. The process of any one of embodiments 1-22, wherein $R^{1a}$ is halogen and $R^{1b}$ is halogen.

Embodiment No 33. The process of any one of embodiments 1-22, wherein $R^{1a}$ and $R^{1b}$ are F.

Embodiment No 34. The process of any one of embodiments 1-33, wherein each $R^2$ is independently hydrogen, halogen, hydroxyl, —CN, or $C_{1-3}$ alkyl.

Embodiment No 35. The process of any one of embodiments 1-34, wherein m is 0.

Embodiment No 36. The process of any one of embodiments 1-34, wherein m is 1.

Embodiment No 37. The process of any one of embodiments 1-34, wherein $R^2$ is halogen or $C_{1-3}$ alkyl and m is 1.

Embodiment No 38. The process of any one of embodiments 1-34, wherein $R^2$ is halogen and m is 1.

Embodiment No 39. The process of any one of embodiments 1-38, wherein the compound of formula (II) is:

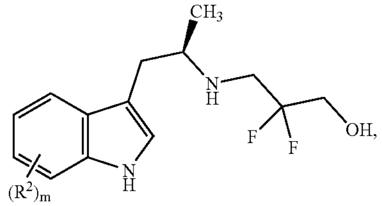

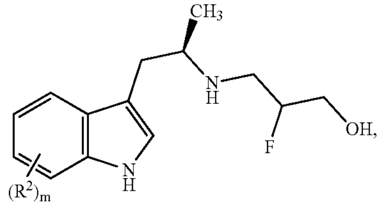

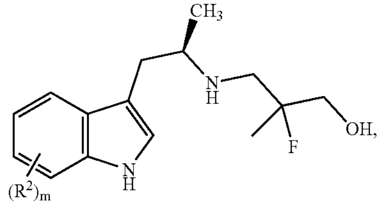

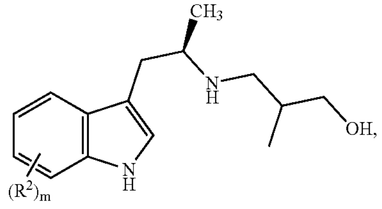

-continued

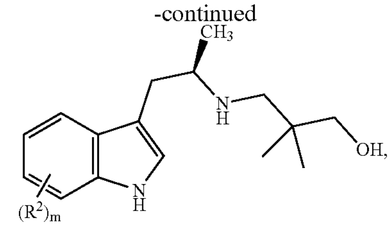

,

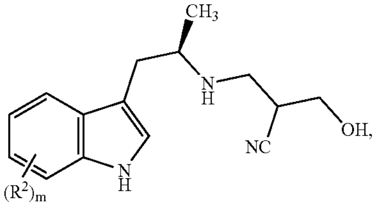

,

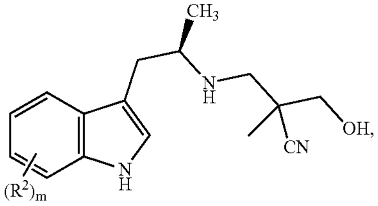

, or

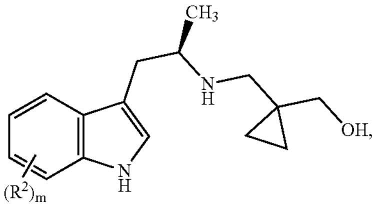

, or a stereoisomer or salt thereof.

Embodiment No 40. The process of any one of embodiments 1-35, wherein the compound of formula (II) is:

(2)

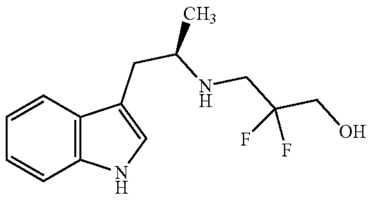

or a salt thereof.

Embodiment No 41. The process of any one of embodiments 1-40, wherein the compound of formula (II) or a stereoisomer or salt thereof is contacted with a compound having formula (X):

(X)

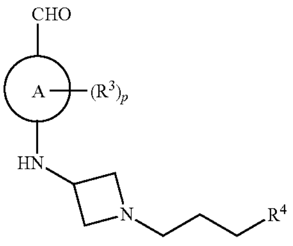

or a stereoisomer or salt thereof ring A is phenyl or pyridinyl;

each $R^3$ is independently hydrogen, halogen, or $C_{1-3}$ alkyl, $R^4$ is halogen or —CN; and p is 1 or 2;

to form a compound of formula (I):

(I)

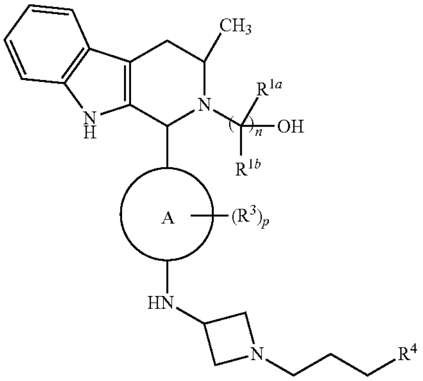

or a stereoisomer or pharmaceutically acceptable salt thereof.

Embodiment No 42. The process of embodiment 41, wherein the compound of formula (X) is:

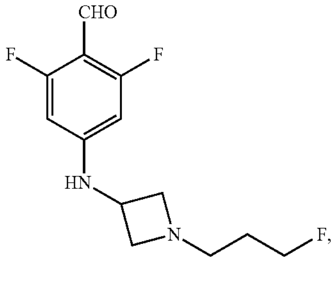

,

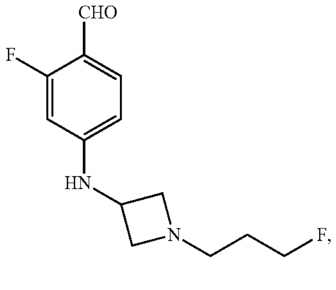

,

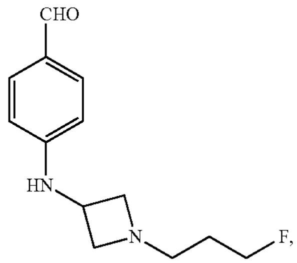

,

-continued
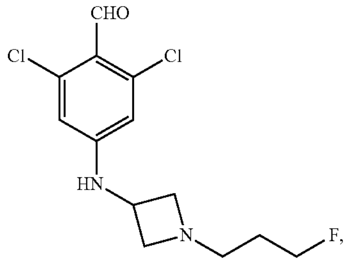
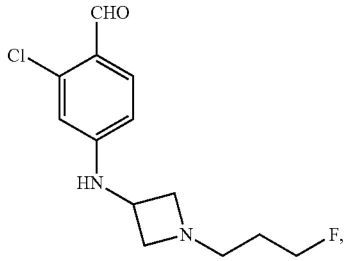
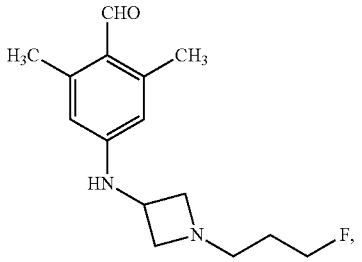
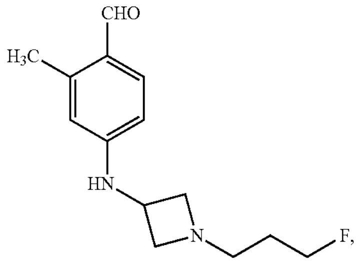
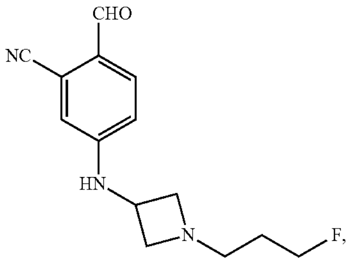
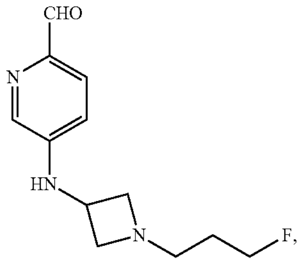
-continued
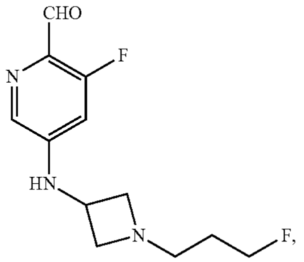
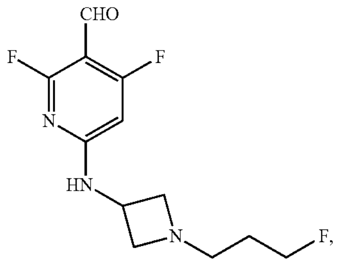
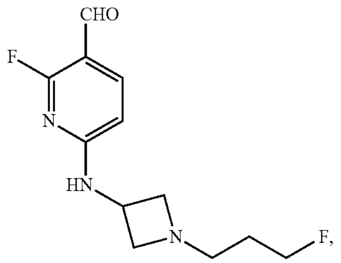
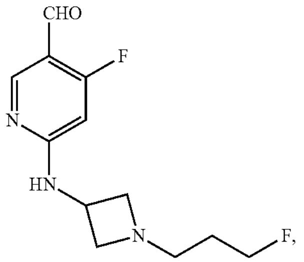
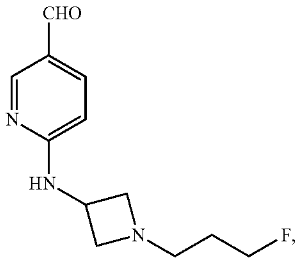
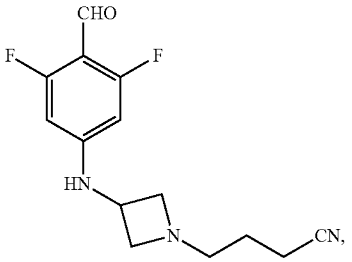

-continued

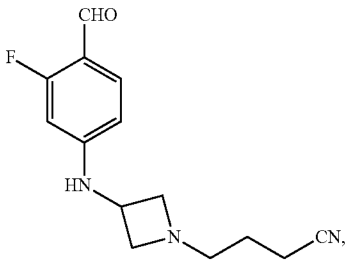

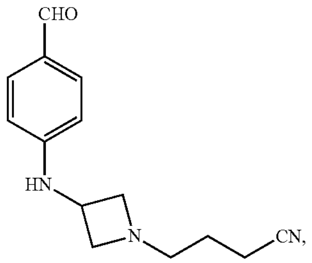

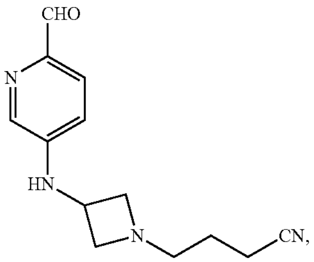

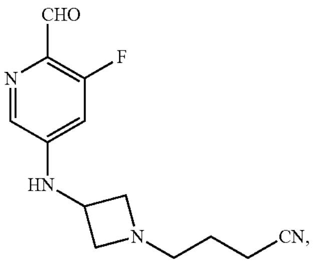

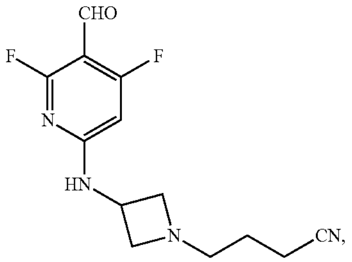

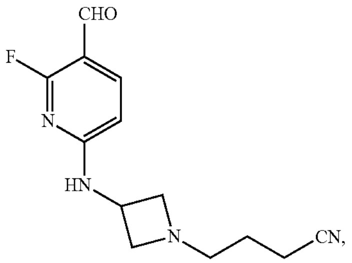

-continued

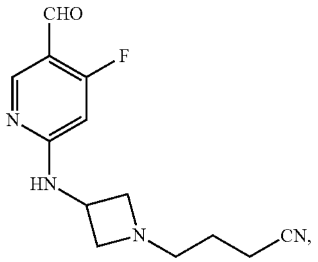

or

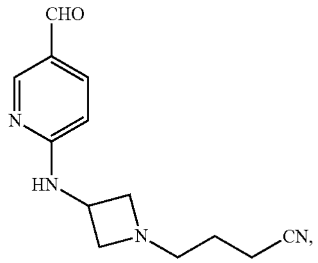

or a salt thereof.

Embodiment No 43. A process for the synthesis of a compound having the formula (1), the process comprising:

(1)

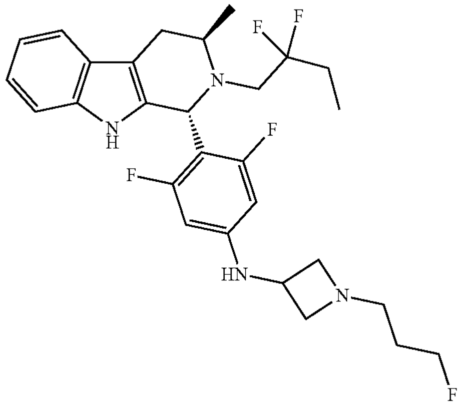

or a pharmaceutically acceptable salt thereof (a) contacting a compound of formula (2)

(2)

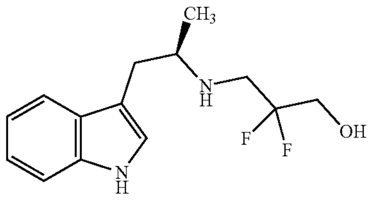

or a salt thereof, wherein the compound of formula (2) is synthesized according to the process of embodiment 1, 8, or 12 and wherein the compound of formula (V) has formula (5)

(5)

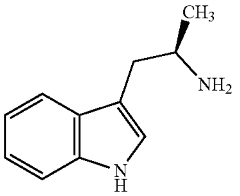

or a salt thereof and the compound of formula (VI) has formula (6):

(6)

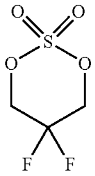

(b) with a compound of formula (10)

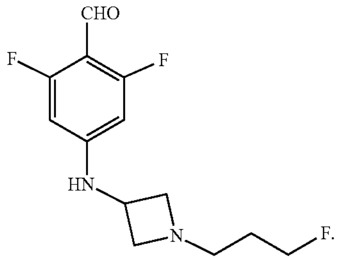 [SMILES: O=Cc1c(F)cc(NC2CN(CCCF)C2)cc1F]

or a salt thereof thereby making a compound of formula (1) or a pharmaceutically acceptable salt thereof.

Embodiment No 44. The process of embodiment 43, wherein the compound of formula (6) is prepared by:

(12a)

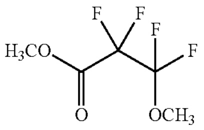

(a) contacting a compound of formula (12a)

(12b)

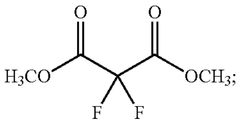

with $H_2SO_4$ to make a compound of formula (b) reducing the compound of formula (12b) to make a compound of formula (12c)

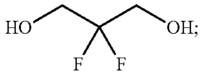

(c) cyclizing the compound of formula in the presence of $SOCl_2$ to make the compound of formula (12d)

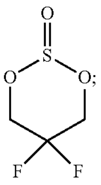

and (d) contacting the compound of formula (12d) with $FeCl_3$, NaOCl and a base, thereby making the compound of formula (6).

The following Examples are presented by way of illustration, not limitation.

EXAMPLES

Synthesis of Compounds described herein. All reagents and solvents were purchased from commercial suppliers and used with no additional purification. Anhydrous solvent (dichloromethane) was utilized. Commercially available solvents were not further purified.

Example 1

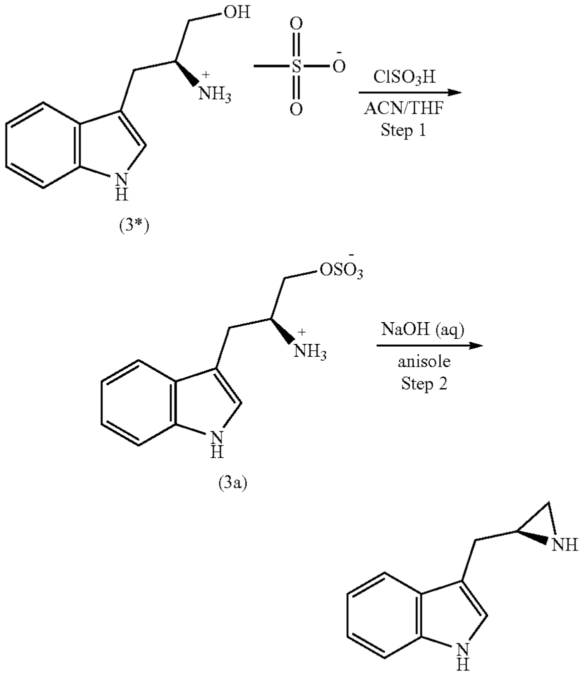

(3*) (3a) (4)

Step 1: (S)-2-ammonio-3-(1H-indol-3-yl)propyl sulfate Compound 3a

Acetonitrile and THF were charged to a reactor and the temperature was set to −5-5° C. Compound 3* (1 equiv.) and $ClSO_3H$ (1.13 equiv.) were alternatively charged to the reaction in 5 portions at −5-5° C. and the reaction was stirred for at least 30 min. The resulting suspension was filtered and the filter cake washed with THF. Reactions were performed at 30 g and 75 kg scale of Compound 3*.

Step 2: (S)-3-(aziridin-2-ylmethyl)-1H-indole Compound 4 The THF wet product 3a was dissolved in 3.1 equiv. aqueous NaOH (10%-w/w) and. Anisole (4V relative to 3*) was added and THF was distilled off until a temperature of 93-97° C. The biphasic reaction mixture was stirred for 5 h at 93-97° C. to effect formation of aziridine 4. The phases were separated and the aqueous layer discarded. To the organic layer was added 1 V butanol (with respect to 3*) and the organic layer was washed twice with water at 65-75° C. 3 V of butanol (with respect to 3*) was added to the organic layer and the solution cooled to 20-30° C. before telescoping into Step 3. Alternatively, following separation of the phases, the organic layer is washed at 30° C. once.

Step 3: (R)-1-(1H-indol-3-yl)propan-2-amine Compound 5

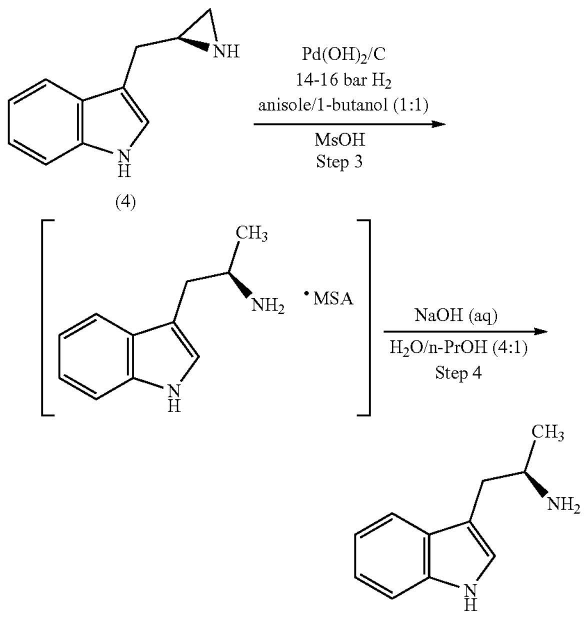

(4)

(5)

Compound 4 telescoped from Step 2 in anisole/1-butanol (1:1-v/v) and $Pd(OH)_2/C$ catalyst (5%-w/w with respect to 3*) were suspended in anisole/1-butanol. After inertisation and change of atmosphere to hydrogen, the temperature was set to 75-85° C. and a hydrogen pressure of 14-16 bar was applied. Hydrogenation was continued for about 2 h at 75-85° C. until complete. Alternatively, a hydrogen pressure of 12 bar was applied and the hydrogenation carried out for 5-6 h. The temperature was set to 20-30° C. and the catalyst was filtered off. The filter cake was washed with butanol and the filtrate is used for further processing.

The product from Step 3 was then crystallized as alpha-mehtyltryptamine mesylate, which purges the majory impurities including dimer byproduct. After concentration of the product solution to remove residual water, methanesulfonic acid (1.05 eq, based on total amount of amine bases) was added over at least 1 h at 75-85° C. The suspension was left for at least 1 h at 75-85° C., cooled to 20-30° C. over at least 2 h and finally left for at least 1 h at 20-30° C. The suspension was filtered and the filter cake washed with anisole/1-butanol (1:1-v/v). Water was applied followed by azeotropic distillation at 90-100° C. and atmospheric pressure. The solution was then cooled to 15-25° C. before adding propanol to give a 4:1-v/v mixture of water/propanol. Sodium hydroxide solution (30% aqueous) was added to a pH of >11 and the suspension was left for at least 1 h at 15-25° C. The suspension was filtered and the filter cake washed with 4:1-v/v water/propanol followed by a slurry wash with water. Dried the product at 35-45° C. in vacuo to afford the final product as a white to slightly yellow solid.

(R)-34(1-(1H-indol-3-yl)propan-2-yl)amino)-2,2-difluoropropan-1-ol Compound 2

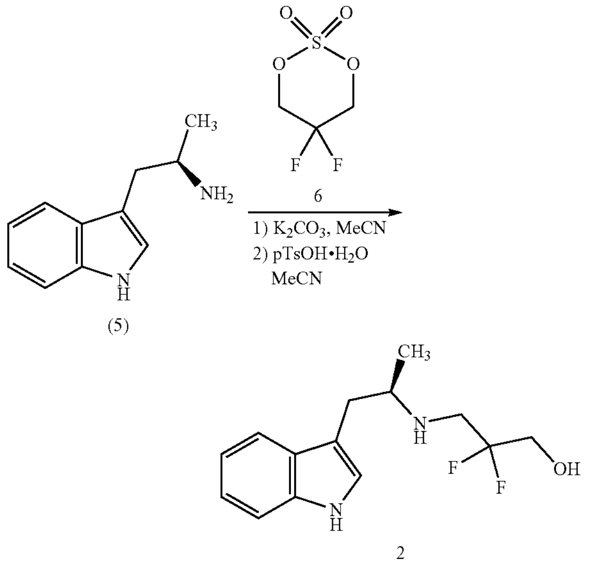

(5)

2

Compound 5 (25 g, 0.14 mol) was mixed with compound 6 (27.0 g, 0.16 mol, 1.10 eq) and 5 volumes acetonitrile (with respect to Compound 5) at internal temperature of 15-25° C. The mixture was heated to internal temperature of 75-85° C. Potassium carbonate (13.8 g, 0.10 mol, 0.7 eq) was added at this temperature in 4 portions over 1 h and the mixture was stirred for another 2 h. Moderate gas development was observed. The conversion was checked. The mixture was then cooled to internal temperature of 30-° C. and filtered. The filter cake was displacement-washed with 25 mL acetonitrile each. Afterwards, the mixture was heated to internal temperature of 75-85° C., a solution of 29.8 g (0.16 mol, 1.1 eq) p-toluenesulfonic acid in 1 volume of deionized water were added during 1 h and the biphasic mixture was stirred for 2 h. The conversion was checked for completeness.

The mixture was then cooled to internal temperature of 0-10° C. and quenched onto 8 volumes of purified water during 10 min. The pH was adjusted to 9 by adding 3.5 volumes of saturated sodium carbonate solution in purified water at internal temperature of 0-10° C. The mixture was then stirred at internal temperature of 0-10° C. for 30 min. A slight gas development was observed. Subsequently, the mixture was warmed to internal temperature of 15-25° C. and the pH was readjusted to 9 using sodium carbonate solution. The mixture was then extracted two times with 5 volumes of isopropyl acetate each at internal temperature of 15-25° C. and the combined organic phases were afterwards washed with 5 volumes of deionized water to remove residual salts. The product stayed in the organic phase. After concentration of the organic phase at internal temperature of and 200-300 mbar to approx. 5 volumes, 16 volumes of methanol were added in parallel to distillation. After distillation of approx. 17 volumes of distillate, the completeness of the solvent swap was checked. Three volumes of purified water were then added at internal temperature of 35-45° C. during at least 1 h and the brown solution was seeded. The crystallization was monitored. After the crystallization started, another 5 volumes of purified water were added at internal temperature of 35-45° C. during at least 1 h, the suspension was cooled to internal temperature of 0-10° C. during at least 2 h and stirred at this temperature for at least 1 h. The wet product was collected by filtration, slurry-washed twice with 2 volumes of purified water each and dried in vacuo at internal temperature of 55-65° C.

Example 2

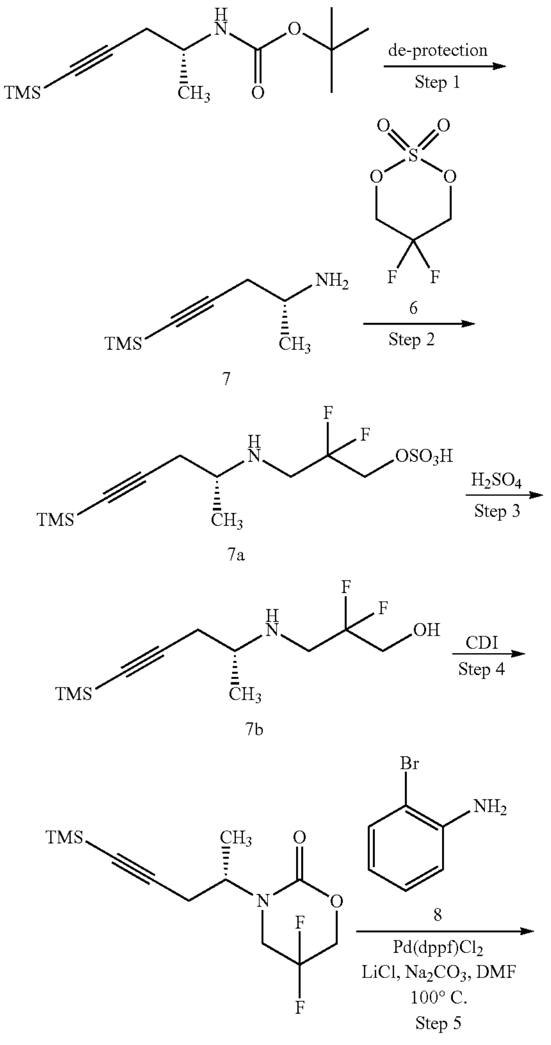

-continued

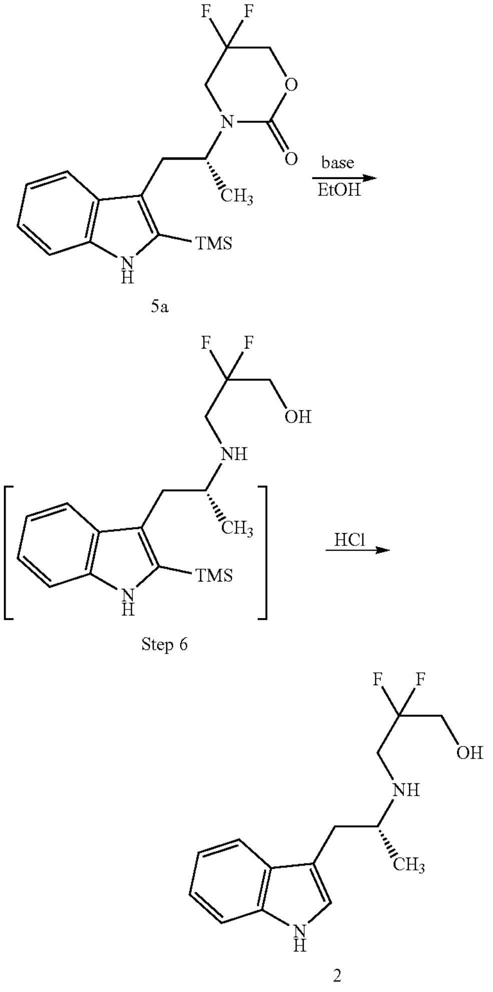

Step 1: (R)-5-(trimethylsilyl)pent-4-yn-2-amine Compound 7

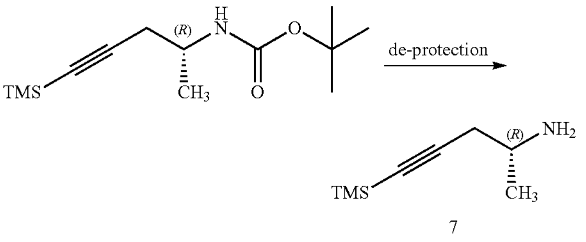

Starting material tert-butyl (R)-(5-(trimethylsilyl)pent-4-yn-2-yl)carbamate (28.6 g, 91.4 A %, 84 wt %, 94.2 mmol, 1.0 equiv.) was dissolved in DCM (140 mL, 5 vol.) and EA (28 mL, 1 vol.). The solution was cooled to 0° C., then TFA (64.4 g, 565.2 mmol, 6.0 equiv.) was added dropwise at 0-5° C. Upon the completion of addition, the mixture was warmed to ambient temperature and stirred for additional 16 h. The reaction mixture was concentrated under vacuum at 38° C. for 1 h to provide ~80.5 g of crude compound 7 (~51 w %) in 89% yield (corrected). The crude product was used to next step without further purification.

Step 2: (R)-2,2-difluoro-3-((5-(trimethylsilyl)pent-4-yn-2-yl)amino)propyl hydrogen sulfate Compound 7a

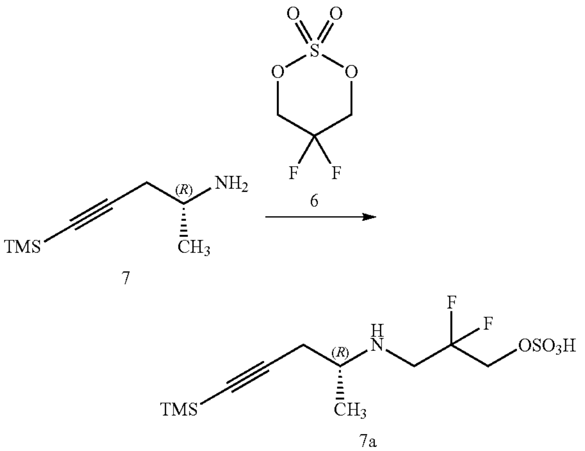
6
7
7a

Toluene (70 mL×3) was added into crude compound. 7 (~67.0 g, 88.6 mmol, 1.0 equiv.). The resulting solution was concentrated under vacuum at 38° C. for 30 min to give ~37.6 g of the crude. The crude was dissolved in MeCN/toluene (210 mL, 10 vol.). The mixture was stirred at 45-50° C. $K_2CO_3$ (30.5 g, 221.5 mmol, 2.5 equiv.) was added portion-wise into the mixture. Compound 6 (15.8 g, 93.0 mmol, 1.05 equiv.) was added. Upon the completion of addition, the mixture was heated to 75-80° C. and stirred for additional 4 h.

10% citric acid (~500 mL) was added to adjust pH=3 ~4 and the mixture was extracted with EtOAc (200 mL×2). The combined organic phase was washed with brine (200 mL) and then dried with $Na_2SO_4$. Filtered and the cake was washed with EA, the combined filtrate & washes was concentrated under vacuum at 38° C. for 30 min to give the crude (~26.0 g, 69.4 wt %).

The crude was slurried in EtOAc/n-heptane (2 vol.: 2 vol., 100 mL) at 0-5° C. for 1 h. Filtered and the cake was washed with EtOAc/n-heptane (1:1, 2 vol., ~50 mL), the cake was dried under vacuum at 38° C. for 2 h, followed by high vacuum drying to provide 15.1 g of cpd. 7a as a pale yellow solid in 50% corrected over three steps.

Step 3: (R)-2,2-difluoro-3-((5-(trimethylsilyl)pent-4-yn-2-yl)amino)propan-1-ol Compound 7b

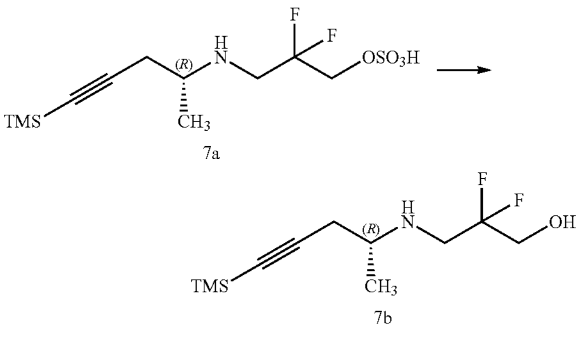
7a
7b

Compound 7a (0754144, 26.0 g, 79.0 mmol, 1.0 equiv.) was dissolved in THF (260 mL, 10 vol.) and then $H_2O$ (17.0 g, 948.0 mmol, 12.0 equiv.) was added. $H_2SO_4$ (7.75 g, 79.0 mmol, 1.0 equiv.) was added drop-wise. The reaction mixture was stirred at 20-25° C. for 16 h.

$Na_2CO_3$ (solid, 5.3 g, 1.5 equiv.) was added, the resulting mixture was stirred at ~25° C. for 10 min. $Na_2SO_4$(15.0 g) was added. The suspension was filtered and the cake was washed with THF (30 mL), the filtrate was concentrated under vacuum to provide 19.4 g of cpd. 7b as a gray jelly in 98% isolated yield.

Step 4: 5,5-difluoro-3-(5-(trimethylsilyl)pent-4-yn-2-yl)-1,3-oxazinan-2-one Compound 7c

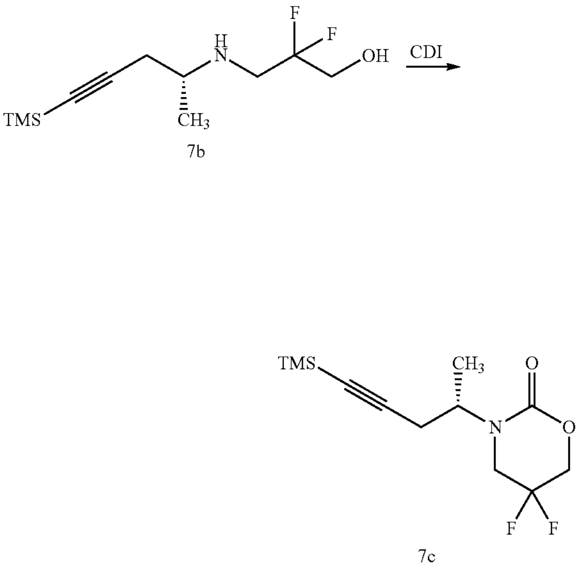

7b
7c

Compound 7b (3.5 g, 14.0 mmol, 1.0 equiv.) was dissolved in THF (35 mL, 10 vol.) under $N_2$. CDI (2.64 g, 15.4 mmol, 1.1 equiv.), DMAP (175 mg, 1.4 mmol, 0.1 equiv.) was added. The reaction mixture was heated to reflux and stirred for 16 h. The mixture was diluted with EtOAc, then the mixture was washed with saturated $NH_4Cl$ solution (50 mL×2).

After phase separation, the organic phase was washed with brine, dried with $Na_2SO_4$. After filtration, the filtrate was concentrated under vacuum to obtained ~5.0 g of crude product. The crude was purified by column (n-heptane/EA=1:0 to 20:1) to provide ~3.4 g of compound 7c in 90% yield (uncorrected).

Step 5: (R)-5,5-difluoro-3-(1-(2-(trimethylsilyl)-1H-indol-3-yl)propan-2-yl)-1,3-oxazinan-2-one Compound 5a

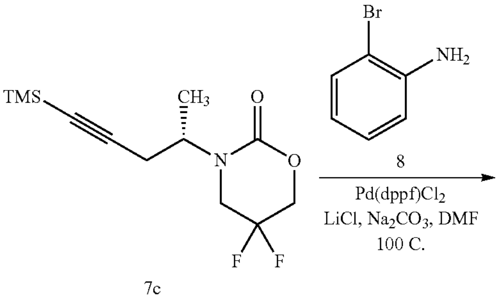

8
7c

-continued

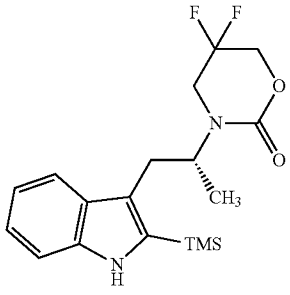

5a

Compound 7c (400 mg, 1.45 mmol, 1.0 equiv.) was dissolved in DMF (8.0 mL, 20 vol.) under $N_2$. $Na_2CO_3$ (307 mg, 2.9 mmol, 2.0 equiv.), LiCl (60 mg, 1.45 mmol, 1.0 equiv.), Pd(dppf)$Cl_2$ (88 mg, 0.12 mmol, 8 mol %) and 2-bromoaniline (300 mg, 1.74 mmol, 1.2 equiv.) was added quickly. The reaction mixture was purged with $N_2$ for 4-5 times, then heated to 100° C. and stirred for 3 h. IPC1.

The reaction mixture was cooled to ~25° C. gradually. EA (50 mL) and brine (50 mL) were added and two phases were separated. The aqueous was extracted with EA (50 mL), then the organic phase was dried over $Na_2SO_4$ and the filtrate was concentrated to dryness. The crude was purified by column to provide ~320 mg of compound 5a (92 A % purity) in ~60% yield (uncorrected).

Step 6: (R)-34(1-(1H-indol-3-yl)propan-2-yl)amino)-2,2-difluoropropan-1-01 Compound 2

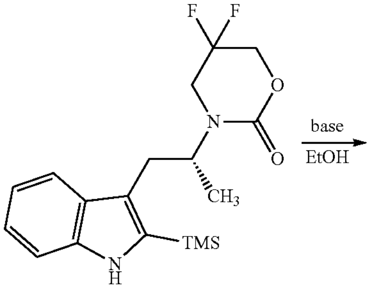

5a

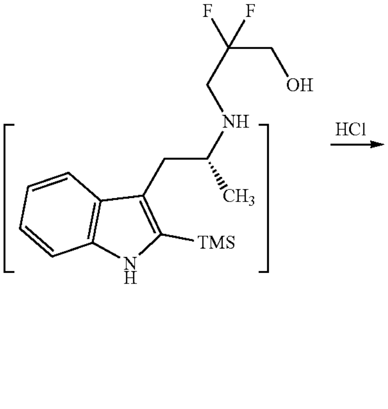

-continued

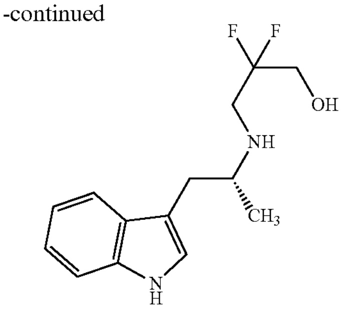

2

Crude 5a (50 mg, 0.14 mmol, 1 equiv.), LiOH·$H_2O$ (15.4 mg, 0.35 mmol, 2.5 equiv.) and $H_2O$ (0.5 mL)/EtOH (0.5 mL) were added to a vial (10 mL). The resulting mixture was heated to 50-55° C. and stirred for 2 h. Aqueous HCl (6N, 0.5 mL) was added to above mixture and the resulting mixture was stirred for 1 h. The mixture was cooled to ~20° C. Filtered and the cake was dried under high vacuum at 35-40° C. for 1 h to provide ~38 mg of crude product (~80 A %) in 100% yield.

Example 3

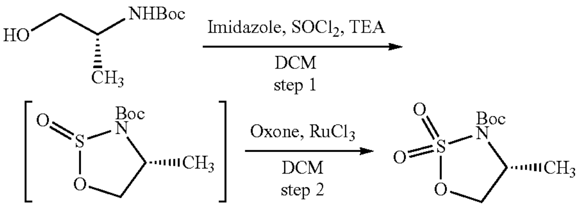

Step 1: tert-butyl (4R)-4-methyl-1,2,3-oxathiazolidine-3-carboxylate 2-oxide

To a solution of imidazole (437 g, 6.4 mol, 1.5 equiv.) in DCM (5.5 L, 7.5 vol.) was added $SOCl_2$ (763 g, 6.4 mol, 1.5 equiv.) dropwise at −5 to 0° C. under $N_2$ in a period of 2 h. The reaction mixture was stirred for 0.5 h at −5 to 0° C. Starting material tert-butyl (R)-(1-hydroxypropan-2-yl)carbamate (740 g, 4.3 mol, 1.0 equiv.) in DCM (5.5 L, 7.5 vol.) was added dropwise at −5 to 0° C. over 2 h. The reaction mixture was stirred for 0.5 h. at −2 to 0° C. $Et_3N$ (865 g, 8.6 mol, 2 equiv.) was added dropwise at −5 to 0° C. and then the mixture was stirred for 2 h.

Upon the completion of reaction, water (6 L) was added at 0-20° C. and two phases were separated. The aqueous was extracted with DCM (5 L). The combined organic phase was washed with 10 w % citric acid (5 L), aq. $NaHCO_3$ (5 L) and brine (5 L). The organic phase was cooled to 0-10° C.

Step 2: tert-butyl (R)-4-methyl-1,2,3-oxathiazolidine-3-carboxylate 2,2-dioxide $H_2O$ (13 L) and $RuCl_3$·x$H_2O$ (9.6 g) was added successively, and then oxone (4.0 kg, 6.4 mol, 1.5 equiv.) was added. The reaction mixture was warmed to 30-33° C. gradually and the reaction was stirred for 4 h. The reaction mixture was filtered through 500 g of celite and the cake was washed with DCM (5 L), two phases (the filtrate) were separated.

Then the aqueous was extracted with DCM, the combined organic phase was washed with sat. $Na_2S_2O_3$ (5 L×3) and brine (5 L×2) and then dried with $Na_2SO_4$ (1 kg). Filtered and the cake was washed with DCM (3 L), the combined filtrate & washes was concentrated under vacuum at 30° C. to provide ~850 g of tert-butyl (R)-4-methyl-1,2,3-oxathiazolidine-3-carboxylate 2,2-dioxide with 98 wt % by qNMR in ~85% isolated yield.

Step 3: tert-butyl (R)-(5-(triethylsilyl)pent-4-yn-2-yl)carbamate

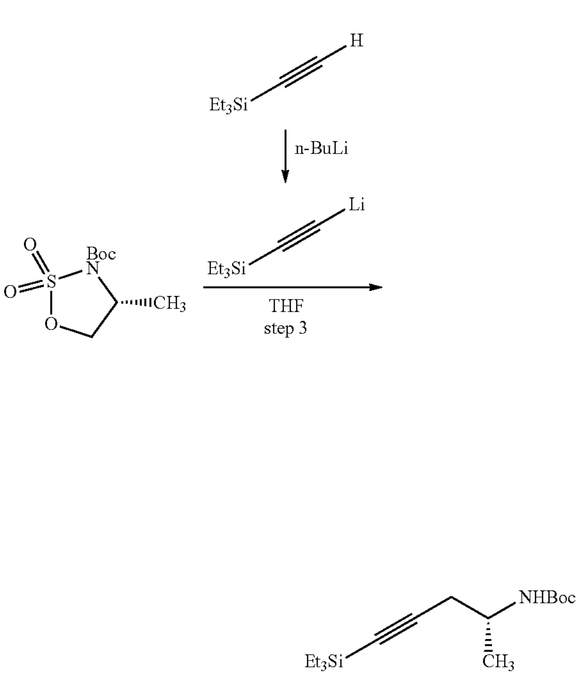

7p

Triethyl(ethynyl)silane (92.6 g, 0.66 mol, 1.3 equiv.) was dissolved in THF (150 mL), then the solution was cooled to −5 to 0° C. n-BuLi (265 mL, 2.5 M, 1.3 equiv.) was added drop-wise over 1 h. The reaction mixture was stirred for 30 min at −5 to 0° C.

Tert-butyl (R)-4-methyl-1,2,3-oxathiazolidine-3-carboxylate 2,2-dioxide (120 g, 0.51 mol, 1.0 equiv.) was dissolved in THF (600 mL) under $N_2$. The reaction mixture was cooled to −10° C. to 0° C. The prepared TESC2Li (~500 mL, 0.66 mol, 1.3 equiv.) was added drop-wise at −10° C. to 0° C. over 1 h. The reaction mixture was stirred for 2 h at −5° C. to 0° C.

The reaction was quenched with saturated $NH_4Cl$ (300 mL) at −10° C. to 0° C. The mixture was separated and the aqueous was extracted with EtOAc (~500 mL×2). The organic phases were combined and washed with brine (500 mL×2). The organic phase was dried with $Na_2SO_4$ (~30 g) and then filtered.

The cake was rinsed with EtOAc (~50 mL×2). The filtrate was concentrated under vacuum at 35° C. for ~2 h to provide about 180 g of crude tert-butyl (R)-(5-(triethylsilyl)pent-4-yn-2-yl)carbamate. The crude tert-butyl (R)-(5-(triethylsilyl)pent-4-yn-2-yl)carbamate was purified by column (silica gel, 200-300 mesh, 6 w) with EtOAc/n-Heptane (0-10%). About 14 L of desired fraction was collected. After concentration under vacuum at 35-40° C., about 105 g of pure tert-butyl (R)-(5-(triethylsilyl)pent-4-yn-2-yl)carbamate (compound 7p) was obtained with 98 A % in 70% isolated yield.

Step 4: (R)-1-(1H-indol-3-yl)propan-2-amine Compound 5

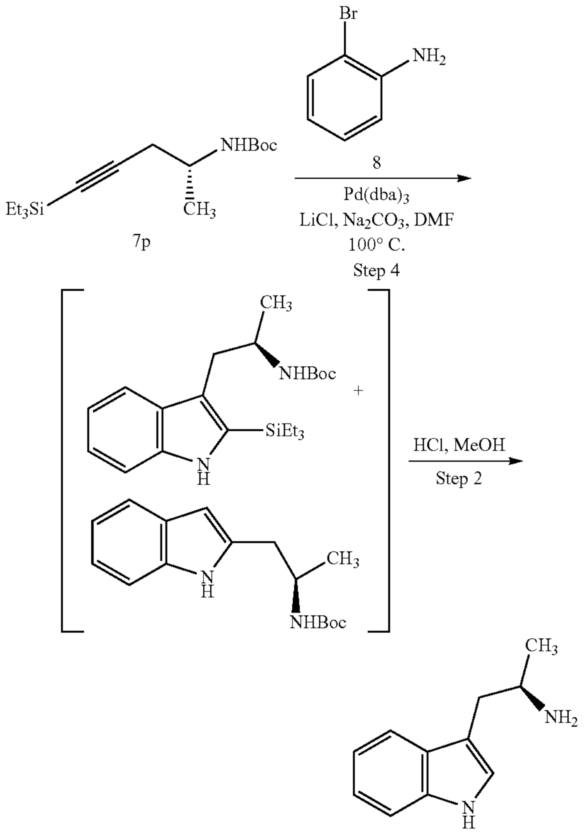

5

Step 4a: tert-butyl (R)-(1-(2-(triethylsilyl)-1H-indol-3-yl)propan-2-yl)carbamate $Na_2CO_3$ (4.5 g, 42 mmol, 2.5 equiv.), $Pd_2(dba)_3$ (0.77 g, 0.84 mmol, 0.05 equiv.), $P(tBu)HBF_4$ (0.48 g, 1.68 mmol, 0.1 equiv.), 2-bromoaniline (4.3 g, 25.2 mmol, 1.5 equiv.) and compound 7p (6.27 g, 16.8 mmol, 1.0 equiv.) were charged into Me-THF (50 mL, 10 vol.) under $N_2$. The reaction mixture was purged with $N_2$ for 4-5 times, heated to reflux and stirred for 24 h. The reaction mixture was cooled to ~25° C., and 100 mL of DCM and 100 mL of $H_2O$ were added.

Two phases were separated and the aqueous was extracted with DCM (~50 mL). The combined organic phase was washed with $H_2O$ (50 mL) and brine (50 mL), and dried with $Na_2SO_4$ (5 g). Filtered and the cake was washed with DCM, the combined washes and filtrate was concentrated under vacuum at 35-40° C. to provide 24.1 g of the crude (20.4 w %) in 75% yield (corrected).

Step 4b: (R)-1-(1H-indol-3-yl)propan-2-amine Compound 5

The crude compound (20.4 w %) dissolved in DCM (50 mL) was washed with about 30 mL of HCl solution (1M) for 4 times. The organic phase was charged into a flask and HCl gas was bubbled at room temperature (~20° C.) for 1 h. About 30 mL of water was added and two phases were separated, the aqueous was extracted with DCM (15 mL×2). The aqueous was adjusted until pH=7-8 with solid NaOH and then extracted with DCM (10 mL).

A solution of NaOH (1.5 g) in water (4 mL) was dropwise into above aqueous under stirring at room temperature (~20° C.). The aqueous was extracted with DCM (50 mL) and the organic phase was concentrated under vacuum at 35° C. to provide about 2.0 g of Compound 5 with 96 A % in 90% isolated yield (uncorrected).

Compound 2 can be made from step 2 according to the methods of Example 1 described herein.

Example 4: 2,2-difluoromalonate Compound 12b

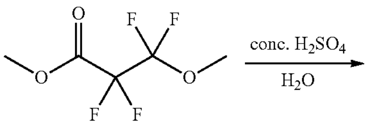

12a

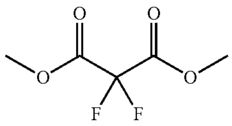

12b

A PTFE bottom reactor was charged with 2 Kg of compound 12a, and 2.1 Kg of concentrated sulfuric acid was added. Then the mixture was heated with stirring for about 4 hours at 45-55° C. (30% aq NaOH scrubber was used to absorb HF generated in the reaction). The mixture was then added dropwise to ice water (5 kg/5 kg). Quench temperature was maintained at 0° C. The organic phase was separated and the aqueous layer was extracted with DCM (2L, 1 V) once. The organic layers were combined together and DCM was removed under vacuum. The crude sample was purified by vacuum distillation. Main fraction of compound 12b was collected at 62-66° C./20 mmHg. $^1H$ NMR (400 MHz, $CDCl_3$): δ=3.89 ppm (s, 6H); $^{13}C$ NMR (100 MHz, $CDCl_3$): δ=53.95 ppm (—$CH_3$), 105.98 ppm (—$CF_2$—, $^1J_{CF}$ 259.1 Hz), 160.94 ppm (—CO—, $^2J_{CF}$ 30.9 Hz); $^{19}F$ NMR (188 MHz, $CDCl_3$): δ=−112.05 ppm (s, 2F).

Example 5

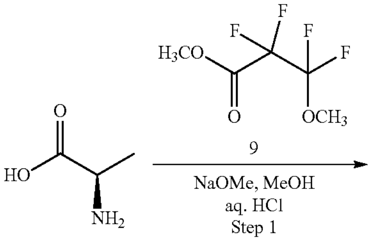

-continued

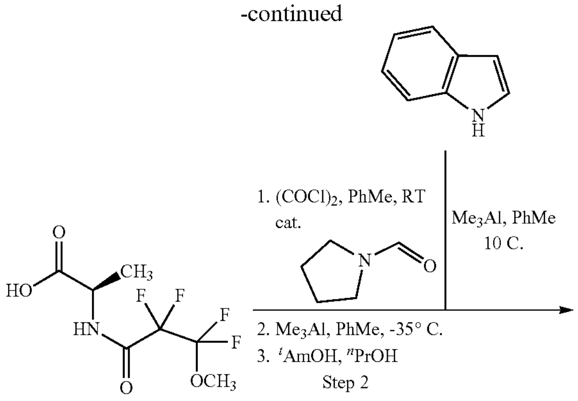

11

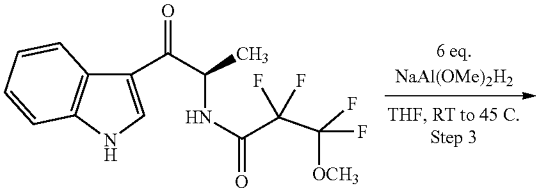

5c

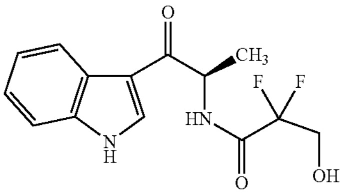

2

Step 1:

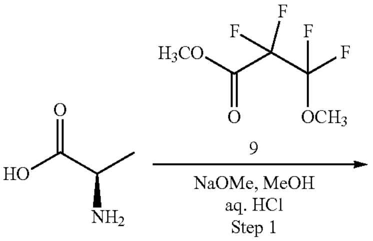

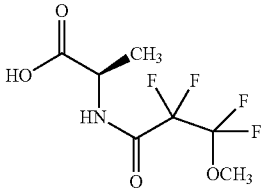

11

To a round bottom flask equipped with a magnetic stirrer was charged alanine (100 g, 1.122 mol, 1.00 equiv) and methanol (150 ml). To the resulting suspension sodium methoxide (30 w % in methanol, 1.235 mol, 1.10 equiv) was added within 2 min. Rinsed the transfer line with methanol (10 ml). Stirred the reaction until fully dissolved and added within 3 min. methyl 2,2,3,3-tetrafluoro-3-methoxypropanoate (173 ml, 1.235 mol, 1.10 equiv). Stirring was continued for 20 minutes, before the reaction mixture was evaporated under reduced pressure to result in a yellow clear oil. The oil was diluted with water, followed by adding 2M aqueous HCl (75 ml, 0.15 mol, 0.13 equiv) resulting a pH of approx. 7.

The solution was transferred into an addition funnel and the flask charged with 105.0 g conc. aq. HCl (37%) (89 ml, 1.066 mol, 0.95 equiv). The content of the addition funnel was added to the aq. HCl under stirring at ambient temperature within 30 min. Water was added during the addition to allow magnetic stirring, as the product suspension gets thicker. The white suspension was stirred for 1 h at ambient temperature before it was filtered. The filter cake was washed with WBI and dried overnight at 10 mbar/70° C. Yield: 266 g (95.9% yield) product as white solid. $^1$H NMR (600 MHz, $CDCl_3$): δ 6.98-6.77 (m, 1H), 4.74-4.65 (m, 1H), 3.71 (s, 3H), 1.56 (d, J=7.2 Hz, 3H); $^{13}$C NMR (151 MHz, $CDCl_3$): δ 175.6, 158.8, 117.4, 108.0, 51.5, 48.3, 17.8.

Step 2:

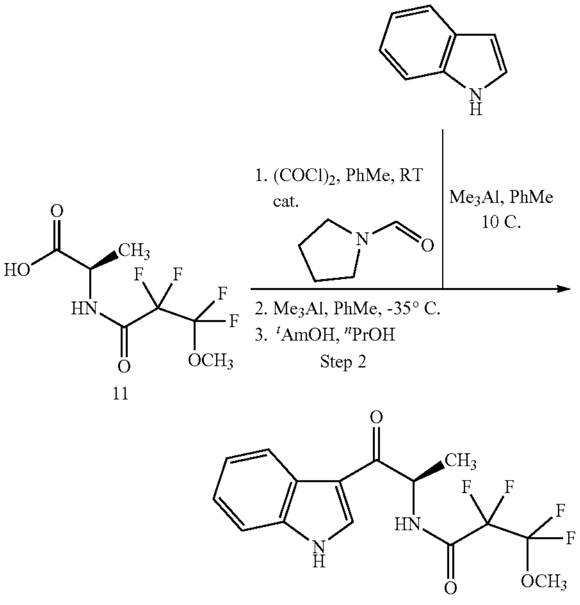

11

5c

Charged a 1000 ml sulfating flask equipped with a mechanical stirrer, addition funnel and an Argon bubbler with Indole (338.3 mmol, 1.045 equiv) and added toluene (120 ml). The mixture was cooled in an ice bath and at internal temperature of <14° C. trimethylaluminum (2M in toluene, 161.8 ml, 323.7 mmol., 1.04 equiv) within 15 min and stirred at <25° C. after the addition is finished until a white suspension was formed.

Equipped a 350 ml sulfating flask equipped with a mechanical stirrer, addition funnel and an argon bubbler. Charged the flask with Compound 11 (323.7 mmol, 1.0 equiv), followed by toluene (80 ml) and N-formyl pyrrolidine (1.15 ml, 12.1 mmol, 0.037 equiv). At 25° C. oxalyl chloride (29.2 ml, 333.4 mmol, 1.03 equiv) was added within 40 min while stirring. The resulting green/yellow turbid solution (approx. 145 ml) was stirred for 25 min until gas evolution ceased and the contents transferred into an addition funnel.

The suspension of dimethylaluminum indolate prepared above was cooled to −30 to −40° C. and the acid chloride solution was added within 10 to 15 min with stirring, so that the temperature of the mixture did not exceed −30° C. After the addition was finished, trimethylaluminum (2M in toluene, 194 ml, 388 mmol, 1.2 equiv) was added between −30 to −40° C. within 23 min and the resulting dark solution was stirred for 2 h at this temperature. Trimethylaluminum (2M in toluene, 20 ml, 40 mmol, 0.12 equiv) was added and stirring continued for 2 h. The reaction mix was cannulated in 15 min into a 1000 ml flask containing t-amylalcohol (181 ml. 1651 mmol. 5.1 equiv) at <15° C.). The resulting product suspension was stirred at 25° C. and heated to 65° C. Heptane (160 ml) was added and the mixture stirred at 65° C. for min. The mixture was cooled to 40° C. and within 20 min 900 n-Propanol (31.8 ml, mmol, equiv) was added. The mixture was cooled to 10° C. and stirred for 10 min.

The mixture was cannulated onto a filter over which a stream of argon was flowing. After filtration, the filter cake was compressed and briefly mother liquor sucked out (−150 ml). The filter cake was washed with toluene (80 ml) and residual mother liquor pushed out using Heptane (80 ml). The filter cake was dried for 15 min (66.9 g) and dried under reduced pressure at 50° C. to yield 65.4 g (58.3% yield) product as an orange-ish solid (98% pure). $^1$H NMR (600 MHz, DMSO-d6): δ 12.07 (br s, 1H), 9.31 (d, J=7.2 Hz, 1H), 8.42 (d, J=3.2 Hz, 1H), 8.19-8.15 (m, 1H), 7.50-7.47 (m, 1H), 7.25-7.22 (m, 1H), 7.22-7.18 (m, 1H), 5.28-5.20 (m, 1H), 3.65 (s, 3H), 1.41 (d, J=7.2 Hz, 3H); $^{13}$C NMR (151 MHz, DMSO-d6): δ 192.3, 157.8, 136.5, 134.0, 125.7, 123.0, 121.9, 121.3, 117.5, 113.1, 112.2, 108.0, 51.7, 51.2, 18.0.

Step 3:

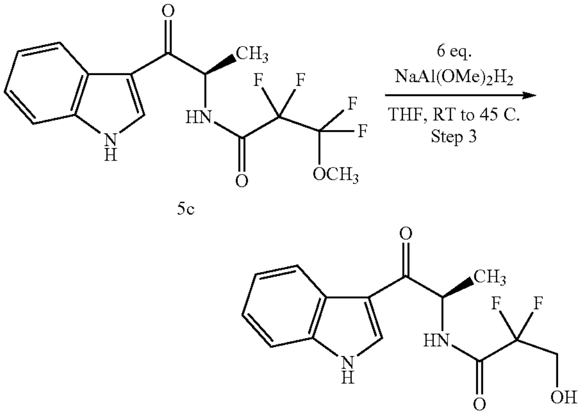

5c

2

Charged a 100 ml Easymax reactor equipped with a mechanical stirrer and an argon bubbler with sodium aluminumhydride and at 25° C. added THF (35 ml). The mixture was stirred for 15 min before a solution of methanol (7.04 ml. 173.3 mmol, 123 equiv) in THF (10 ml) was added within 30 min at <45° C. IT along the walls of the reactor. The resulting off-white suspension was stirred for 5 min, before a solution of (R)—N-(1-(1H-indol-3-yl)-1-oxopropan-2-yl)-2,2,3,3-tetrafluoro-3-methoxypropanamide (14.44 mmol, 1.00 equiv, Compound 5c)) in THF (20 ml) is added 5 within 30 min at <35° C. The resulting yellowish suspension was heated to 45° C. within 30 min and stirred for 19 h.

Sodium Sulfate (36.1 mmol, 2.50 equiv) was added to the reaction mixture, followed by a solution of water (6.50 ml, 361 mmol, 25.0 equiv) in THF (13.5 ml) which was added with 400 rpm stirring within 20 min allowing the temperature to rise. The resulting greyish suspension was heated to reflux and the solvent partially exchanged at ambient pressure and constant volume to toluene (50 ml). After the exchange was complete, the suspension was cooled to 25° C. within 50 min, filtered and the filter cake washed with ethyl acetate (20 ml).

10% aq. sulfuric acid (6.0 ml, 6.54 mmol, 0.45 equiv) was added until the resulting aqueous phase had a pH of 2.1. The organic phase was washed with water (8 ml) and the water acidified with a few drops of 10% aq. Sulfuric acid until a pH of 2.1 was reached. The combined aqueous phases were washed with two portions each of ethyl acetate (20 ml) and once with heptane (20 ml). To the aqueous phase was added 2M aq. NaOH (7.22 ml, 14.44 mmol, 1.00 equiv) until a pH 5.3. After stirring for 5 min, NaOH addition was continued over at least two hours until the pH of the resulting yellowish suspension stays constant at pH 6.5 for at least 30 min The suspension was cooled to 4° C. 15, stirred for 1 h, filtered and the filter cake washed after compaction with cold water (5 ml)16 and cold water/MeOH=10/1 (5 ml). The filter cake was dried under reduced pressure over night to result in an off white solid (2.685 g, 69.3% yield, 99.3% pure). $^{1}H$ NMR (600 MHz, $CDCl_3$): δ 8.06 (br s, 1H), 7.58 (dd, J=7.9, 0.9 Hz, 1H), 7.38 (dt, J=8.2, 0.9 Hz, 1H), 7.21 (ddd, J=8.1, 7.1, 1.1 Hz, 1H), 7.13 (ddd, J=7.9, 7.0, 1.0 Hz, 1H), 7.03 (d, J=2.3 Hz, 1H), 3.93-3.74 (m, 2H), 3.26-3.15 (m, 1H), 3.15-3.02 (m, 2H), 2.95-2.78 (m, 2H), 1.17 (d, J=6.3 Hz, 3H); $^{13}C$ NMR (101 MHz, $CDCl_3$) δ=136.41, 127.58, 122.88, 122.57, 122.23, 120.46, 119.51, 118.84, 118.03, 112.62, 111.28, 65.12 (t, J=31.7 Hz, 1C), 53.46, 50.59 (t, J=29.0 Hz, 1C), 32.85, 20.39.

Example 6

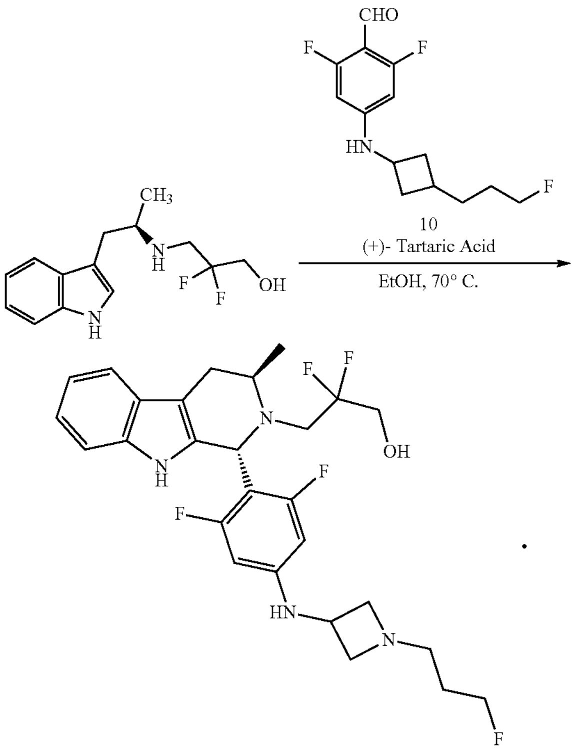

A

-continued

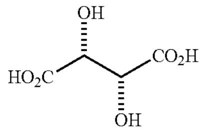

Charged an inertized reactor with Compound 10 (25.0 g, 91.8 mmol, 1.00 equiv) and added Compound 2 (30.8 g 114.8 mmol, 1.25 equiv), followed by L-(+)-Tartaric Acid (20.67 g, 137.7 mmol, 1.50 equiv). Added ethanol and heated the reaction mixture to 69-72° C. Stirred for about 2 h before adding Compound A seed crystals (308.8 mg). Stirred the mixture for about 46h.

Added EtOH (95.8 mL) and stirred for 15 min. Cooled the mixture in about 1 h to 15-25° C. and stirred at this temperature for about 2h. Filtered the suspension, rinsed the reactor with a spray ball using EtOH (95.8 mL) and washed the filter cake with two portions of EtOH. Dried the filter cake at 50° C. under vacuum. Compound A was isolated in ~80% yield as pale brown powder.

The invention claimed is:

1. A process for the preparation of a compound of formula (II):

(II)

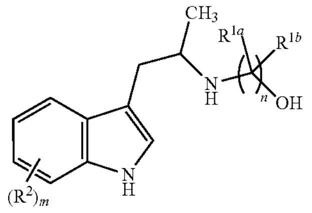

or a stereoisomer thereof, wherein:

each $R^{1a}$ is independently hydrogen, halogen, unsubstituted $C_{1-3}$ alkyl, unsubstituted $C_{1-3}$ haloalkyl, or unsubstituted $C_{1-3}$ alkoxy;

each $R^{1b}$ is independently hydrogen, halogen, unsubstituted $C_{1-3}$ alkyl, unsubstituted $C_{1-3}$ haloalkyl, or unsubstituted $C_{1-3}$ alkoxy;

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy;

m is 0, 1, or 2; and n is 1, 2, or 3;

wherein the process comprises the following steps:

(a) contacting a compound of formula (III):

(III)

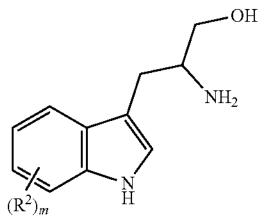

or a salt or stereoisomer thereof, wherein:

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy; and m is 0, 1, or 2;

with a sulfonic acid selected from the group consisting of $H_2SO_4$ and $ClSO_3H$, to form a compound of formula (IIIa):

(IIIa)

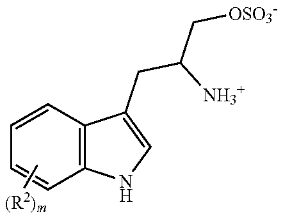

or a salt or stereoisomer thereof, wherein:

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy; and m is 0, 1, or 2;

(b) contacting the compound of formula (Ma) of step (a), or a salt or stereoisomer thereof, with a base, to form a compound of formula (IV):

(IV)

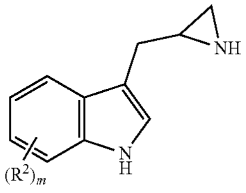

or a salt or stereoisomer thereof, wherein:

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy; and m is 0, 1, or 2;

(c) hydrogenating the compound of formula (IV) of step (b), or a salt or stereoisomer thereof, in the presence of a catalyst, to form a compound of formula (V):

(V)

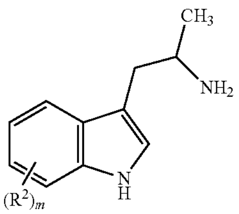

or a salt or stereoisomer thereof, wherein:

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy; and m is 0, 1, or 2; and (d) contacting the compound of formula (V) of step (c), or a salt or stereoisomer thereof, with a compound of formula (VI):

(VI)

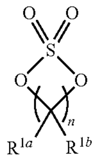

or a stereoisomer thereof, wherein:

each $R^{1a}$ is independently hydrogen, halogen, unsubstituted $C_{1-3}$ alkyl, unsubstituted $C_{1-3}$ haloalkyl, or unsubstituted $C_{1-3}$ alkoxy;

each $R^{1b}$ is independently hydrogen, halogen, unsubstituted $C_{1-3}$ alkyl, unsubstituted $C_{1-3}$ haloalkyl, or unsubstituted $C_{1-3}$ alkoxy; and n is 1, 2, or 3;

thereby forming the compound of formula (II) above, or a stereoisomer thereof.

2. The process of claim 1, wherein the compound of formula (III), or a salt or stereoisomer thereof, is a mesylate salt of formula (III*):

(III*)

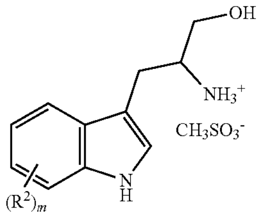

or a stereoisomer thereof, wherein:

each $R^2$ is independently halogen, cyano, unsubstituted $C_{1-3}$ alkyl, unsubstituted $C_{1-3}$ haloalkyl, hydroxyl, or unsubstituted $C_{1-3}$ alkoxy; and m is 0, 1, or 2.

3. The process of claim 2, wherein the mesylate salt of formula (III*), or a stereoisomer thereof, is the mesylate salt of a compound of formula (3*), formula (3x*), formula (3y*), or formula (3z*):

(3*)

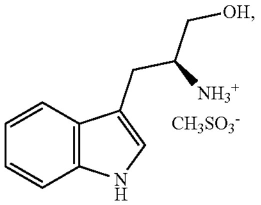

-continued (3x*)

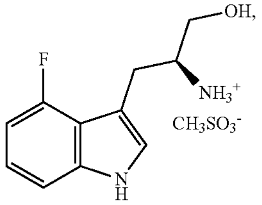

(3y*)

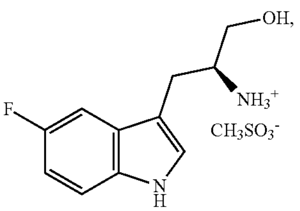

or (3z*)

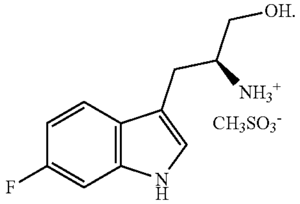

4. The process of claim 2, wherein the mesylate salt of formula (III*), or a stereoisomer thereof, is the mesylate salt of a compound of formula (3*):

(3*)

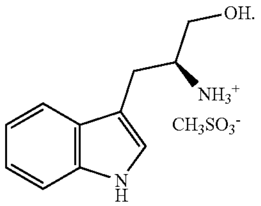

5. The process of claim 1, wherein the sulfonic acid of step (a) is $ClSO_3H$.

6. The process of claim 1, wherein the base of step (b) is a hydroxide base.

7. The process of claim 6, wherein the base of step (b) is KOH, NaOH, or LiOH.

8. The process of claim 1, wherein the catalyst of step (c) comprises Pd, Pt, or Ni.

9. The process of claim 8, wherein the catalyst of step (c) is Pd/C, Pt/C, or Raney Ni.

10. The process of claim 1, wherein the hydrogenation of step (c) is performed in the presence of isopropanol, formic acid, formate, or ammonium.

11. The process of claim 1, wherein the compound of formula (VI) of step (d) is:

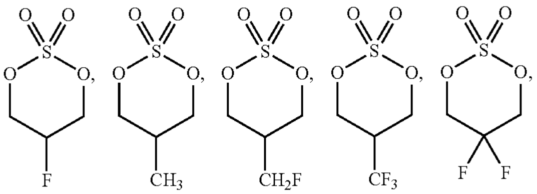

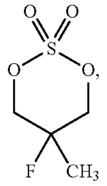

or

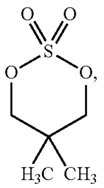

or a stereoisomer thereof.

12. The process of claim 1, wherein:
each $R^{1a}$ is independently hydrogen, halogen, or methyl; and
each $R^{1b}$ is independently hydrogen, halogen, or methyl.

13. The process of claim 1, wherein:
each $R^{1a}$ is independently hydrogen; and
each $R^{1b}$ is independently halogen.

14. The process of claim 1, wherein:
each $R^{1a}$ is independently hydrogen; and
each $R^{1b}$ is independently methyl.

15. The process of claim 1, wherein:
each $R^{1a}$ is independently halogen or methyl; and
each $R^{1b}$ is independently halogen or methyl.

16. The process of claim 1, wherein:
each $R^{1a}$ is independently halogen; and
each $R^{1b}$ is independently halogen.

17. The process of claim 1, wherein:
each $R^{1a}$ is independently F; and
each $R^{1b}$ is independently F.

18. The process of claim 1, wherein:
each $R^{1a}$ is independently halogen; and
each $R^{1b}$ is independently methyl.

19. The process of claim 1, wherein each $R^2$ is independently halogen, cyano, unsubstituted $C_{1-3}$ alkyl, or hydroxyl.

20. The process of claim 1, wherein m is 0.

21. The process of claim 1, wherein m is 1.

22. The process of claim 1, wherein:
$R^2$ is halogen or unsubstituted $C_{1-3}$ alkyl; and
m is 1.

23. The process of claim 1, wherein:
$R^2$ is halogen; and
m is 1.

24. The process of claim 1, wherein the compound of formula (II) is of the following formula:

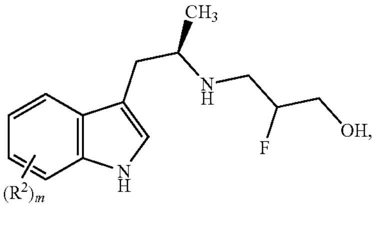

-continued
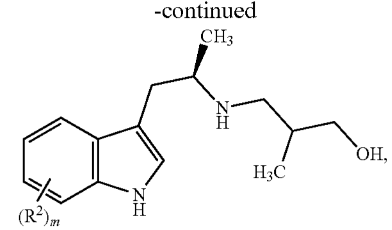
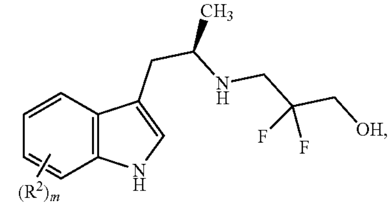
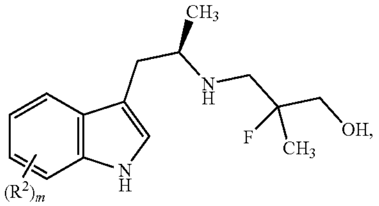
or
-continued
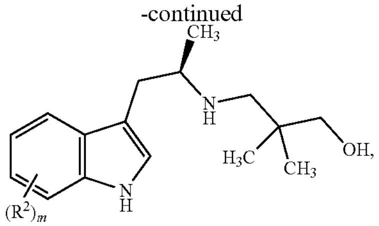
or a stereoisomer thereof.
25. The process of claim 1, wherein the compound of formula (II) is:
(2)
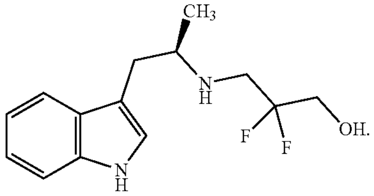
* * * * *